US011304812B1

(12) United States Patent
Khalid

(10) Patent No.: US 11,304,812 B1
(45) Date of Patent: Apr. 19, 2022

(54) METHOD OF FABRICATING OR MODIFYING AN IMPLANT

(71) Applicant: Syed Khalid, Niles, IL (US)

(72) Inventor: Syed Khalid, Niles, IL (US)

( * ) Notice: Subject to any disclaimer, the term of this patent is extended or adjusted under 35 U.S.C. 154(b) by 368 days.

(21) Appl. No.: 16/282,430

(22) Filed: Feb. 22, 2019

Related U.S. Application Data

(60) Provisional application No. 62/634,434, filed on Feb. 23, 2018.

(51) Int. Cl.
| | | |
|---|---|---|
| *A61B 34/10* | (2016.01) | |
| *A61F 2/30* | (2006.01) | |
| *A61B 34/20* | (2016.01) | |
| *A61F 2/28* | (2006.01) | |

(52) U.S. Cl.
CPC .......... *A61F 2/30942* (2013.01); *A61B 34/10* (2016.02); *A61B 34/20* (2016.02); *A61F 2/2875* (2013.01); *A61B 2034/104* (2016.02); *A61B 2034/108* (2016.02); *A61B 2034/2051* (2016.02); *A61B 2034/2055* (2016.02);
(Continued)

(58) Field of Classification Search
CPC .... A61F 2/30942; A61F 2/2875; A61B 34/10; A61B 34/20
See application file for complete search history.

(56) References Cited

U.S. PATENT DOCUMENTS

| | | |
|---|---|---|
| 10,842,504 B2 | 11/2020 | Gordon et al. |
| 2008/0269588 A1 | 10/2008 | Csavoy et al. |

(Continued)

FOREIGN PATENT DOCUMENTS

| | | |
|---|---|---|
| WO | 2016/086054 A1 | 6/2016 |

OTHER PUBLICATIONS

Egger, J., et al., "Interactive Reconstructions of Cranial 3D Implants Under MeVisLab as an Alternative to Commercial Planning Software", PLoS ONE, Mar. 6, 2017, vol. 12(3), pp. 1-20, e0172694, doi:10.1371/journal.pone.0172694.

(Continued)

*Primary Examiner* — Si Ming Ku
(74) *Attorney, Agent, or Firm* — McDonnell Boehnen Hulbert & Berghoff LLP

(57) ABSTRACT

The present disclosure relates to methods of; non-transitory, computer-readable media for; and systems for fabricating or modifying an implant. One example embodiment includes a method. The method includes registering a plurality of intraoperative locations of a surgically resected anatomical region of a patient. The method also includes generating, based on the registered plurality of intraoperative locations, a two-dimensional representation of the registered plurality of intraoperative locations. Further, the method includes determining, based on the two-dimensional representation, a two-dimensional shape of an anatomical feature excised from the surgically resected anatomical region. In addition, the method includes determining, based on the two-dimensional shape of the anatomical feature and a three-dimensional model of a portion of the patient that contains the surgically resected anatomical region, a three-dimensional shape of the anatomical feature. Still further, the method includes fabricating or modifying an implant based on the three-dimensional shape of the anatomical feature.

25 Claims, 28 Drawing Sheets

(52) U.S. Cl.
CPC .............. *A61B 2034/2068* (2016.02); *A61F 2002/30948* (2013.01)

(56) References Cited

U.S. PATENT DOCUMENTS

| | | | |
|---|---|---|---|
| 2008/0269600 A1* | 10/2008 | Csavoy | A61B 90/18 600/426 |
| 2009/0043556 A1 | 2/2009 | Axelson et al. | |
| 2015/0045897 A1 | 2/2015 | Gordon et al. | |
| 2017/0000566 A1 | 1/2017 | Gordon et al. | |
| 2017/0252169 A1* | 9/2017 | Alambeigi | A61B 34/10 |
| 2020/0197182 A1 | 6/2020 | Alambeigi et al. | |

OTHER PUBLICATIONS

Parthasarathy, J., "3D Modeling, Custom Implants and its Future Perspectives in Craniofacial Surgery", Annals of Maxillofacial Surgery, Jan.-Jun. 2014, vol. 4(1), pp. 9-18, doi:10.4103/2231-0746.133065.

Sundseth, J., et al., "Prefabricated Patient-Matched Cranial Implants for Reconstruction of Large Skull Defects", Journal of Central Nervous System Disease, 2013, vol. 5, pp. 19-24, doi:10.4137/JCNSD.S11106.

"CranialMap® 3.0—Integrated Navigation Software Solution", Stryker Navigation, 2017, pp. 1-4.

"Kelyniam: Product Fit", 2017, https://www.kelyniam.com/productfit. (Abstract only).

"Mimics", https://en.wikipedia.org/wiki/Mimics, pp. 1-3, [Accessed from the internet on Jan. 12, 2018].

"OsiriX—The World Famous Medical Imaging Viewer", http://www.osirix-viewer.com, pp. 1-6, [Accessed from the internet on Jan. 12, 2018].

"Surgical Navigation Systems—StealthStation", Medtronic, http://www.medtronic.com/us-en/healthcare-professionals/products/neurological/surgical-navigation-systems/stealthstation.html, pp. 1-5, [Accessed from the internet on Jan. 12, 2018].

* cited by examiner

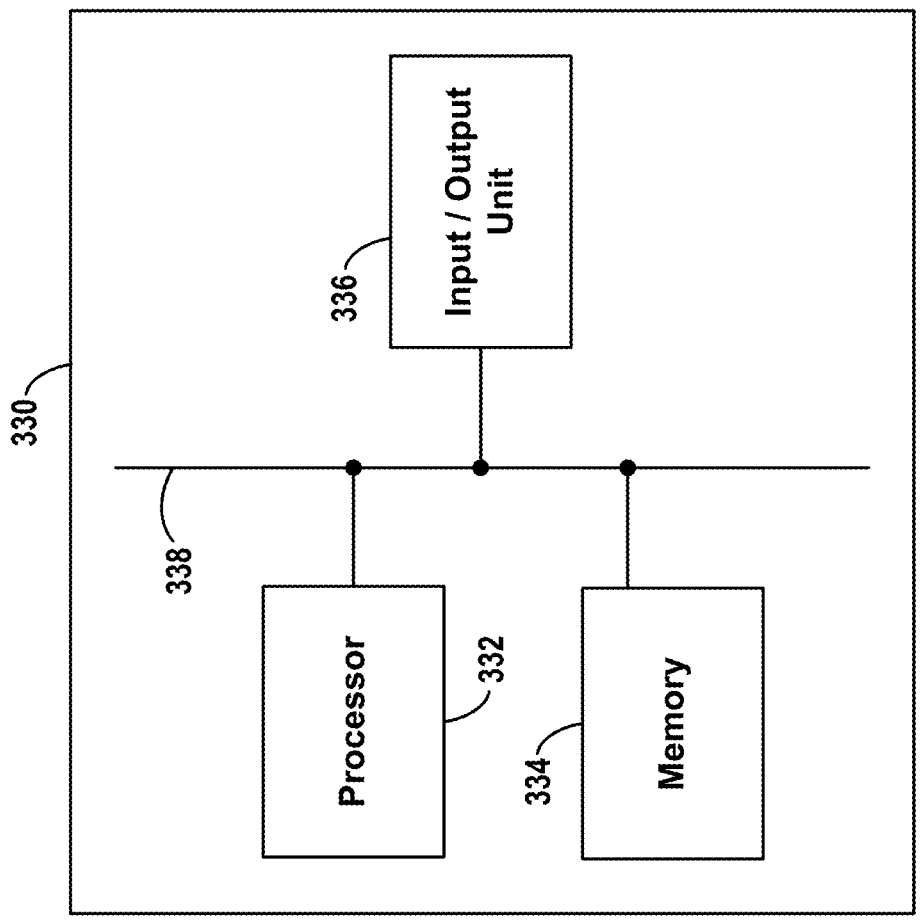

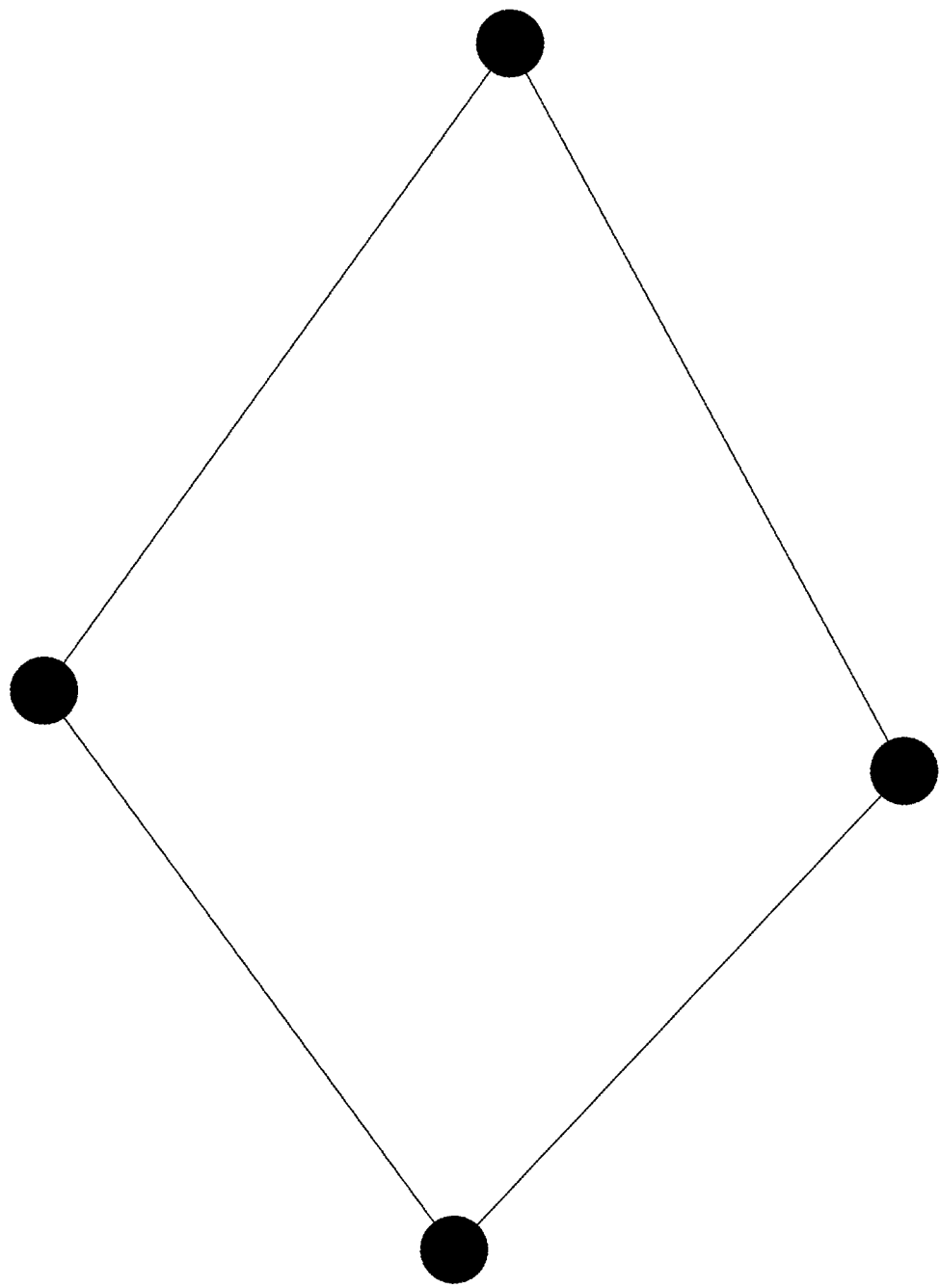

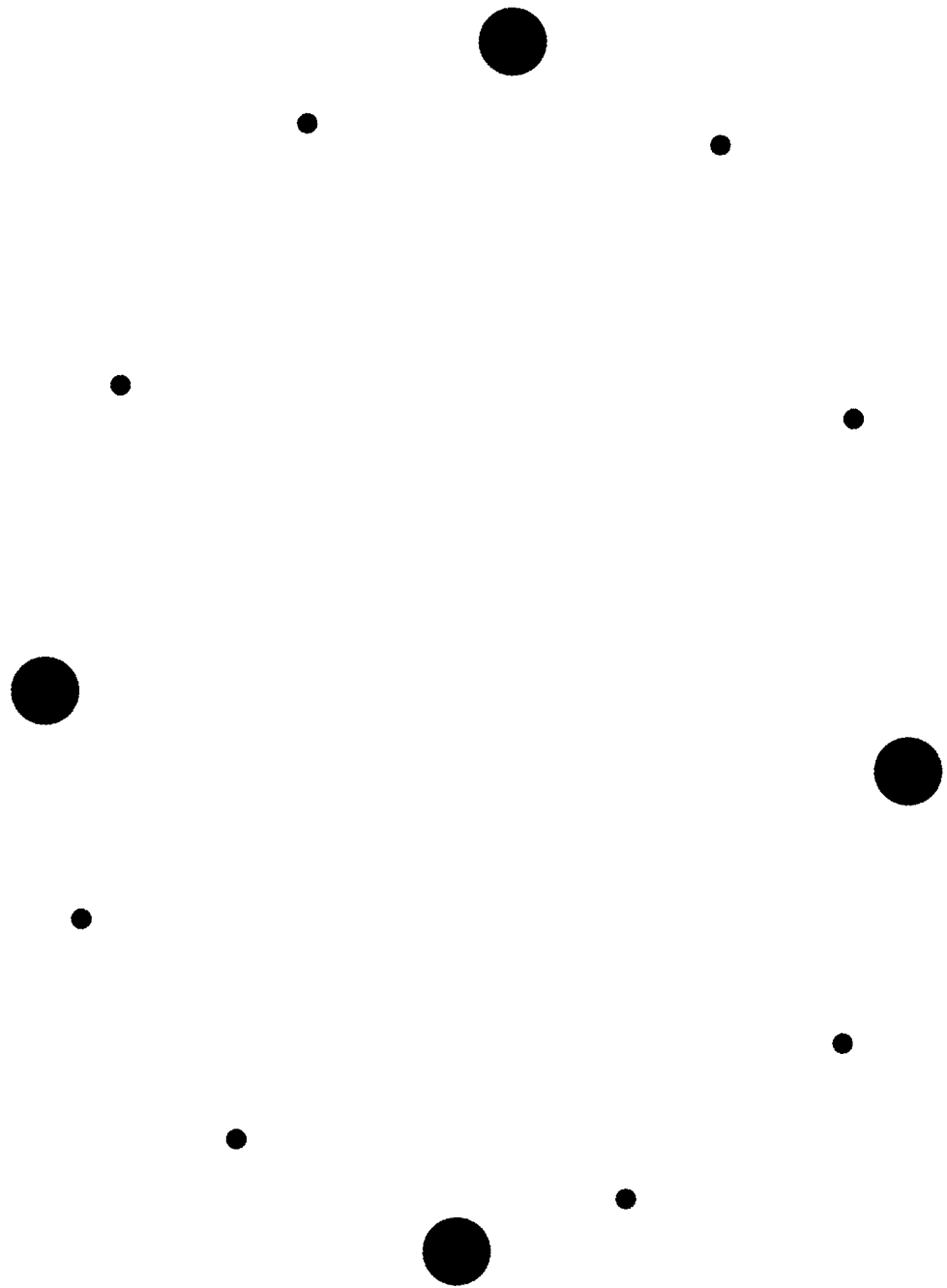

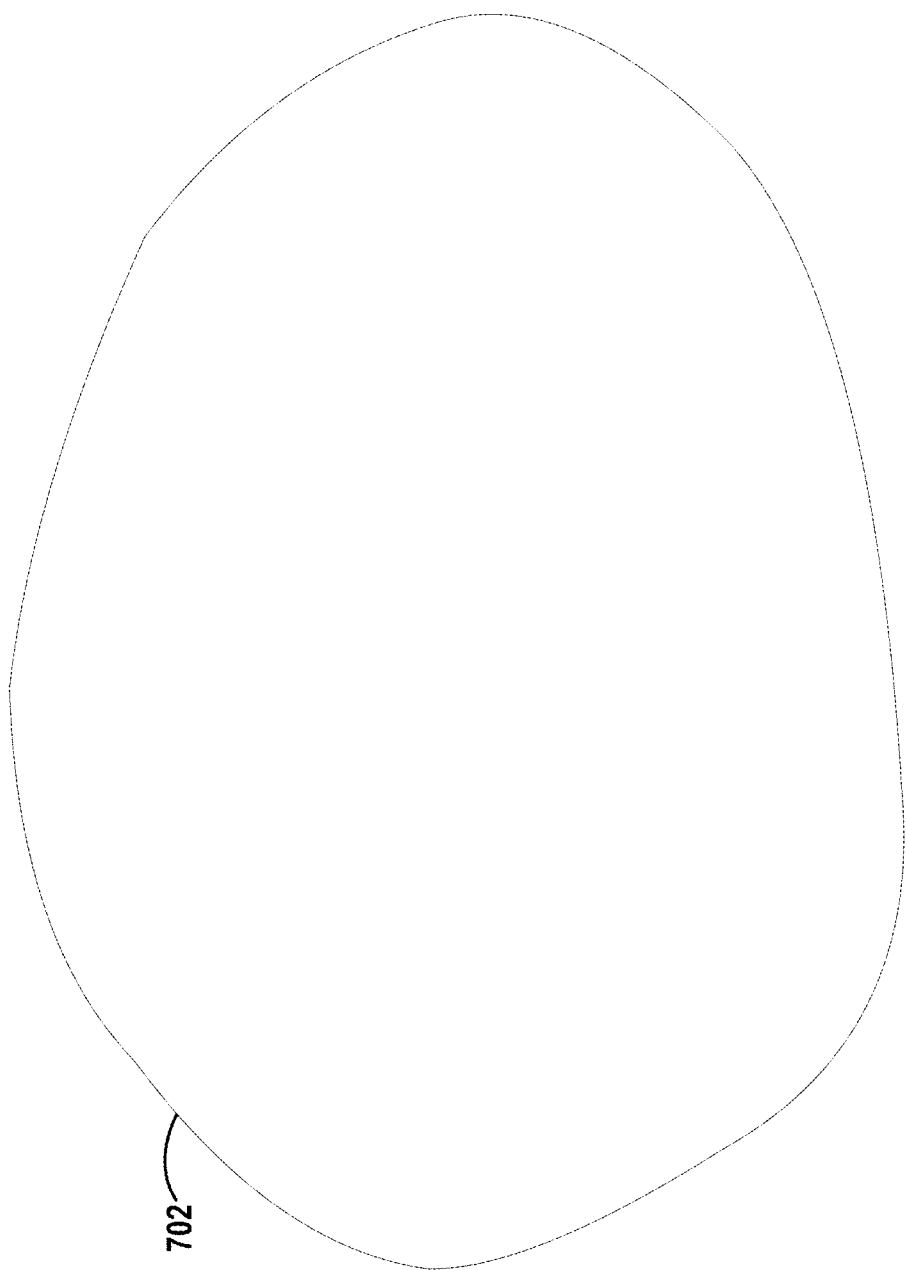

METHOD OF FABRICATING OR MODIFYING AN IMPLANT

CROSS-REFERENCE TO RELATED APPLICATIONS

The present application claims priority to U.S. Provisional Patent Application No. 62/634,434 filed on Feb. 23, 2018, the contents of which are hereby incorporated by reference.

BACKGROUND

Unless otherwise indicated herein, the materials described in this section are not prior art to the claims in this application and are not admitted to be prior art by inclusion in this section.

Implants are used to replace one or more biological structures within a patient. Such devices may be implanted in patients where the biological structure of the patient is damaged or unhealthy. For example, during a cranioplasty, a surgeon may remove a deformity within a patient's skull (e.g., cranium). After resecting the deformed or damaged portion of the cranium, the surgeon may insert a cranial implant in the location of the excised biological substrate. The insertion of the cranial implant may provide stability and protection to the patient. Implants may be used in human patients and animal patients (e.g., dogs, cats, horses, etc.). While conventional methods for replacing one or more biological structures within a patient with an implant might be known, it is understood that methods for improving the design and/or fabrication of implants are ripe for improvement.

SUMMARY

The specification and drawings disclose embodiments that relate to a method of fabricating or modifying an implant.

In a first aspect, the disclosure describes a method. The method includes registering a plurality of intraoperative locations of a surgically resected anatomical region of a patient. The method also includes generating, based on the registered plurality of intraoperative locations, a two-dimensional representation of the registered plurality of intraoperative locations. Further, the method includes determining, based on the two-dimensional representation, a two-dimensional shape of an anatomical feature excised from the surgically resected anatomical region. In addition, the method includes determining, based on the two-dimensional shape of the anatomical feature and a three-dimensional model of a portion of the patient that contains the surgically resected anatomical region, a three-dimensional shape of the anatomical feature. Still further, the method includes fabricating or modifying an implant based on the three-dimensional shape of the anatomical feature.

In some embodiments of the first aspect, the method may include orienting the implant relative to the portion of the patient that contains the surgically resected anatomical region. Further, the method may include implanting the implant in the patient.

In some embodiments of the first aspect, the method may include, prior to fabricating or modifying the implant, scaling the three-dimensional shape of the anatomical feature by a scaling factor such that the implant is smaller in size than the surgically resected anatomical region.

In some embodiments of the first aspect, the three-dimensional may include a computerized tomography (CT) model or a magnetic resonance imaging (MRI) model.

In some embodiments of the first aspect, determining the three-dimensional shape of the anatomical feature may include performing a voxel-additive technique corresponding to regions of the three-dimensional model having a signal value above a threshold signal value that corresponds to bone.

In some embodiments of the first aspect, at least one of the plurality of intraoperative locations may include a burr hole drilled during excision of the surgically resected anatomical region of the patient.

In some embodiments of the first aspect, at least one of the plurality of intraoperative locations may include a point along which a cut was made between adjacent burr holes during excision of the surgically resected anatomical region of the patient. In addition, determining the two-dimensional shape of the anatomical feature or determining the three-dimensional shape of the anatomical feature may include defining edges of the two-dimensional shape or edges of the three-dimensional shape, respectively, based on the cut between adjacent burr holes.

In some embodiments of the first aspect, registering the plurality of intraoperative locations of the surgically resected anatomical region of the patient may include transmitting the plurality of intraoperative locations to a computing device. Further, generating the two-dimensional representation of the registered plurality of intraoperative locations may be performed by the computing device. In addition, determining the two-dimensional shape of the anatomical feature excised from the surgically resected anatomical region may be performed by the computing device. Yet further, determining the three-dimensional shape of the anatomical feature may be performed by the computing device.

In some embodiments of the first aspect, registering the plurality of intraoperative locations may include, for each of the plurality of intraoperative locations, placing an intraoperative probe at the respective intraoperative location. Further, registering the plurality of intraoperative locations may include, for each of the plurality of intraoperative locations, transmitting a three-dimensional location of the intraoperative probe to the computing device.

In some embodiments of the first aspect, each of the plurality of intraoperative locations may include a respective burr hole drilled during excision of the surgically resected anatomical region of the patient. In addition, registering the plurality of intraoperative locations may include, for each of the plurality of intraoperative locations, placing an intraoperative probe at a first location on a circumference of a circle corresponding to the respective burr hole. Still further, registering the plurality of intraoperative locations may include, for each of the plurality of intraoperative locations, transmitting a first three-dimensional location of the intraoperative probe to the computing device. Still yet further, registering the plurality of intraoperative locations may include, for each of the plurality of intraoperative locations, placing the intraoperative probe at a second location on the circumference of the circle corresponding to the respective burr hole. Even still yet further, registering the plurality of intraoperative locations may include, for each of the plurality of intraoperative locations, transmitting a second three-dimensional location of the intraoperative probe to the computing device. Still even yet further, registering the plurality of intraoperative locations may include, for each of the plurality of intraoperative locations, determining, by the computing device, a center of the circle corresponding to the respective burr hole.

In some embodiments of the first aspect, the second location may be on a diameter of the circle corresponding to the respective burr hole opposite the first location.

In some embodiments of the first aspect, registering the plurality of intraoperative locations may include receiving, by the computing device, an image of the surgically resected anatomical region of the patient. Further, registering the plurality of intraoperative locations may also include identifying, by the computing device according to a computer-vision algorithm, each of the plurality of intraoperative locations within the image.

In some embodiments of the first aspect, generating the two-dimensional representation of the registered plurality of intraoperative locations may include projecting each of the registered intraoperative locations onto a two-dimensional plane. Further, determining the two-dimensional shape of the anatomical feature may include identifying, by the computing device, two or more closed polygons each having as their vertices each of the registered plurality of intraoperative locations projected onto the two-dimensional plane. In addition, determining the two-dimensional shape of the anatomical feature may include displaying, by the computing device, each of the two or more closed polygons. Even further, determining the two-dimensional shape of the anatomical feature may include receiving, by the computing device, a selection of which of the two or more closed polygons corresponds to the two-dimensional shape of the anatomical feature excised from the surgically resected anatomical region.

In some embodiments of the first aspect, generating the two-dimensional representation of the registered plurality of intraoperative locations may include projecting each of the registered intraoperative locations onto a two-dimensional plane. Further, determining the two-dimensional shape of the anatomical feature may include identifying, by the computing device, two or more closed polygons each having as their vertices each of the registered intraoperative locations projected onto the two-dimensional plane. In addition, determining the two-dimensional shape of the anatomical feature may include comparing, by the computing device, each of the two or more closed polygons to previously determined two-dimensional shapes of other anatomical features excised from other surgically resected anatomical regions. Yet further, determining the two-dimensional shape of the anatomical feature may include determining, by the computing device based on the comparison, which of the two or more closed polygons have a threshold probability of corresponding to the two-dimensional shape of the anatomical feature excised from the surgically resected anatomical region.

In some embodiments of the first aspect, the other anatomical features excised from the other surgically resected anatomical regions may correspond to additional anatomical features excised from one or more additional surgically resected anatomical regions of the patient.

In some embodiments of the first aspect, wherein the other anatomical features excised from the other surgically resected anatomical regions may correspond to similar anatomical features excised from one or more similar surgically resected anatomical regions of one or more other patients.

In some embodiments of the first aspect, the other anatomical features excised from the other surgically resected anatomical regions may have been excised by a surgeon. Further, the surgeon may have also excised the anatomical feature excised from the surgically resected anatomical region of the patient.

In some embodiments of the first aspect, generating the two-dimensional representation of the registered plurality of intraoperative locations may include projecting each of the registered intraoperative locations onto a two-dimensional plane. Further, determining the two-dimensional shape of the anatomical feature may include identifying a closed polygon having as its vertices each of the registered intraoperative locations projected onto the two-dimensional plane. Additionally, no edges of the closed polygon may intersect one another.

In some embodiments of the first aspect, the anatomical feature excised from the surgically resected anatomical region may be a portion of a cranium of the patient.

In some embodiments of the first aspect, the anatomical feature excised from the surgically resected anatomical region may be a maxillofacial portion of the patient.

In some embodiments of the first aspect, the method may include defining, within the three-dimensional shape of the anatomical feature, a location configured to house a medical device usable to monitor or treat the patient.

In some embodiments of the first aspect, defining, within the three-dimensional shape of the anatomical feature, the location configured to house the medical device usable to monitor or treat the patient may include determining an optimized position for the medical device within the three-dimensional shape of the anatomical feature based on a function of the medical device, a shape of the medical device, a size of the medical device, an orientation of the medical device, a shape of the surgically resected anatomical portion, a size of the surgically resected anatomical portion, or an orientation of the surgically resected anatomical portion.

In some embodiments of the first aspect, the medical device may include an Ommaya reservoir, one or more electrodes of a neurostimulator, one or more electrodes of a deep-brain stimulator, an intake to a fluid conduit leading to a cerebral balloon used to modulate blood flow or flow of spinal fluid, a medication pump, a microprocessor, a memory, a battery, a sensor, a heart pacemaker, a piece of spinal-fusion hardware, an intrauterine device (IUD), a piece of traumatic fracture repair hardware, a coronary stent, a tympanostomy tube, a stent, a vascular graft, an electrode, an infrared sensor, an infrared light, an accelerometer, a cellular device, a thermometer, an intracranial pressure monitor, a blood-pressure monitor, a blood-oxygen monitor, a vascular-flow monitor, a breast implant, an implantable cardioverter defibrillator (ICD), a spine screw, a spine rod, an artificial disk, a metal screw, a metal pin, a metal plate, a metal rod, or a stimulator.

In some embodiments of the first aspect, fabricating or modifying the implant may include incorporating, based on the three-dimensional model, materials of differing densities Into the implant to mimic differing biological substrates of the anatomical feature excised from the surgically resected anatomical region.

In some embodiments of the first aspect, at least one of the biological substrates may include soft tissue.

In some embodiments of the first aspect, modifying the implant based on the three-dimensional shape of the anatomical feature may include projecting an outline of the anatomical feature onto the implant. Further, modifying the implant based on the three-dimensional shape of the anatomical feature may include removing portions of the implant lying outside of the outline of the anatomical feature projected onto the implant.

In some embodiments of the first aspect, fabricating the implant based on the three-dimensional shape of the anatomical feature may include printing the implant using additive manufacturing.

In a second aspect, the disclosure describes a non-transitory, computer readable medium having instructions stored therein, wherein the instructions, when executed by a processor, include receiving a registered plurality of intraoperative locations of a surgically resected anatomical region of a patient. The instructions also include generating, based on the registered plurality of intraoperative locations, a two-dimensional representation of the registered plurality of intraoperative locations. Further, the instructions include determining, based on the two-dimensional representation, a two-dimensional shape of an anatomical feature excised from the surgically resected anatomical region. In addition, the instructions include determining, based on the two-dimensional shape of the anatomical feature and a three-dimensional model of a portion of the patient that contains the surgically resected anatomical region, a three-dimensional shape of the anatomical feature. Still further, the instructions include outputting the three-dimensional shape. The three-dimensional shape is usable to fabricate or modify an implant such that the implant is implantable into the surgically resected anatomical region of the patient.

In a third aspect, the disclosure describes a system. The system includes a device configured to register a plurality of intraoperative locations of a surgically resected anatomical region of a patient. The system also includes a computing device. The computing device is configured to receive the registered plurality of intraoperative locations from the intraoperative probe. The computing device is also configured to generate, based on the registered plurality of intraoperative locations, a two-dimensional representation of the registered plurality of intraoperative locations. Further, the computing device is configured to determine, based on the two-dimensional representation, a two-dimensional shape of an anatomical feature excised from the surgically resected anatomical region. In addition, the computing device is configured to determine, based on the two-dimensional shape of the anatomical feature and a three-dimensional model of a portion of the patient that contains the surgically resected anatomical region, a three-dimensional shape of the anatomical feature. Still further, the computing device is configured to determine output the three-dimensional shape. The three-dimensional shape is usable to fabricate or modify an implant such that the implant is implantable into the surgically resected anatomical region of the patient.

In some embodiments of the third aspect, the device configured to register a plurality of intraoperative locations may include one or more intraoperative probes, one or more cameras, one or more light emitters, or one or more light detectors.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 3B is a schematic illustration of a computing device, according to example embodiments.

FIG. 6C is an illustration of a possible two-dimensional shape of an anatomical feature excised from a surgically resected anatomical region based on a two-dimensional representation of intraoperative locations, according to example embodiments.

FIG. 7A is an illustration of a two-dimensional representation of intraoperative locations, according to example embodiments.

FIG. 7D is an illustration of a possible two-dimensional shape of an anatomical feature excised from a surgically resected anatomical region based on a two-dimensional representation of intraoperative locations, according to example embodiments.

DETAILED DESCRIPTION

Figure 1:
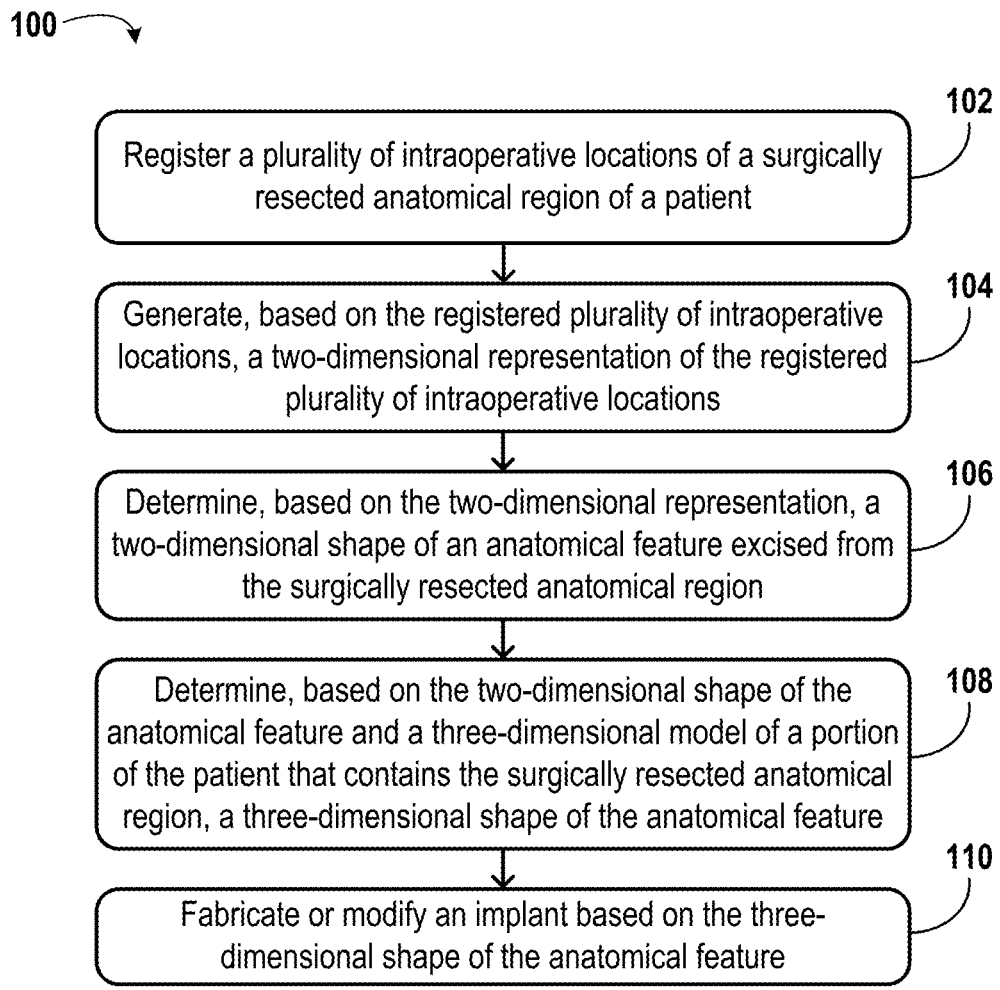
FIG. 1 is an illustration of a method, according to example embodiments.

Example methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the figures should not be viewed as limiting. It should be understood that other embodiments might include more or less of each element shown in a given figure. In addition, some of the illustrated elements may be combined or omitted. Similarly, an example embodiment may include elements that are not illustrated in the figures.

I. OVERVIEW

Example embodiments relate to a method of fabricating or modifying an implant. The methods described herein may be used to create implants or prostheses that can replace one or more surgically resected anatomical regions of a patient. For example, a portion of a leg, arm, skull, hand, finger, foot, toe, knee, chest, back, spine, or any other biological substrate could be replaced with one or more of the implants described herein. Biological substrates, as described herein, include any organic matter that makes up a portion of an organism (e.g., any cell, collection of cells, tissue, organ, system, or collection of systems that make up a portion of an organism). Such biological substrates can include hard tissue, such as bone, or soft tissue, such as ligaments or muscle, for example. It is understood that the methods described herein could be attributed to an implant for any biological substrate in any patient (e.g., animal or human). Even further, implants may be used for a variety of reasons. For example, implants may be cosmetic, contraceptive, orthopedic, sensory/neurological, and/or cardiovascular.

In one example embodiment, a method is described. The method may include recording (e.g., by a surgeon or nurse) multiple locations on a surgically resected portion of a patient. Using a cranioplasty as an example, a surgeon may first remove a portion of the skull (e.g., cranium). Then, using an intraoperative probe, the surgeon may record a plurality intraoperative locations inside, outside, and/or around the removed portion of the skull. For example, if one or more burr holes were drilled to remove the portion of the skull, the surgeon may record the locations of one or more of the burr holes. Each of the intraoperative locations may include a respective set of three-dimensional (3D) coordinates. Such 3D coordinates may be based on the position and/or orientation of the intraoperative probe at the time the respective intraoperative location was registered. Further, the position and/or orientation of the intraoperative probe may be determined by the probe itself (e.g., using sensors such as accelerometers) and/or by a receiver, such as an infrared sensor, configured to monitor the intraoperative probe.

After the 3D intraoperative locations are recorded (e.g., registered) by the surgeon, they may be transmitted to a computing device (e.g., wirelessly from the intraoperative probe). For example, each of the intraoperative locations could be transmitted together or each intraoperative location could be transmitted individually once it is recorded. Once the 3D coordinates of each desired intraoperative locations have been recorded, a two-dimensional (2D) representation of the plurality of intraoperative locations may be made (e.g., by a computing device). This may include projecting the 3D coordinates of the intraoperative locations onto a 2D plane.

Once a 2D representation is generated, the 2D shape of the anatomical feature may be determined based on the 2D representation (e.g., by a computing device). This may include determining a polygon (e.g., a closed, convex polygon) whose outline includes each of the intraoperative locations. In other words, each of the intraoperative locations may be a vertex of a polygon that represents the 2D shape of the anatomical feature. For example, if three burr holes were recorded as intraoperative locations, a triangle may be determined to be the 2D shape of the anatomical feature. However, in some cases, there could be multiple possible 2D shapes of the anatomical features based on the registered intraoperative locations (i.e., multiple polygons that could potentially correspond to the 2D shape). To determine which is the proper 2D shape in such cases, a surgeon could choose the proper shape among a variety of possible shapes, additional intraoperative locations could be registered to eliminate erroneous 2D shapes from the possible shapes, and/or prior anatomical feature shapes removed from a given patient and/or by a given surgeon could be used to refine the set of possible shapes.

After determining the 2D shape of the anatomical feature, a 3D shape of the anatomical feature that was surgically resected from the patient may be determined. Determining the 3D shape could include overlaying the 2D shape on a 3D model of the patient's skull (e.g., a computerized tomography (CT) model, a magnetic resonance imaging (MRI) model, and/or a computer-aided design (CAD) model). Once a 3D shape of the anatomical feature has been determined, an implant can be fabricated and/or modified according to that 3D shape. For example, the implant may be made using additive manufacturing (e.g., 3D-printed) or may be cut down from a previously fabricated, oversized implant. After generating the implant, the implant may be oriented properly with respect to the patient and implanted into the patient.

The method outlined above and further detailed in the remainder of this disclosure with reference to the figures may provide an improvement to implant technology. For example, in some alternative methods of providing implants (e.g., during a cranioplasty), a patient may either be given a standardized implant, which is not tailored to the particular shape of the patient's anatomy and therefore does not necessarily have an appropriate size, shape, and/or fit, or a patient may have a customized implant made after the original surgery to resect the damaged anatomical region. However, if the customized implant is made after the original surgery (e.g., based on CT data or MM data recorded during the surgery), this may take a significant amount of time, thereby requiring the patient to be closed up and an additional surgery being used to implant the patient with the customized implant. This can add excessive cost and/or risk/burden to the patient.

The embodiments described herein allow for a "single-stage" (i.e., within a single operation rather than multiple operations) removal/implant procedure. For example, a patient could have the damaged anatomical region removed, intraoperative locations could be registered, a 3D shape of the removed region could be developed, and an implant could be fabricated/modified according to that 3D shape. This may all be done within an amount of time such that within a single surgery the patient can receive a customized implant. The ability to perform a "single-stage" removal/implant procedure with a customized implant allows for a reduction in risk to the patient, reduction in hardship to a patient (e.g., reduced time away from work due to multiple surgeries), and/or a reduction in cost (e.g., because fewer time in the operating room is required and/or because protective gear for the patient in between operations is not required).

II. EXAMPLE METHODS

The following description and accompanying drawings will elucidate features of various example embodiments. The embodiments provided are by way of example, and are not intended to be limiting. As such, the dimensions of the drawings are not necessarily to scale.

FIG. 1 is an illustration of a method 100, according to example embodiments. The method 100 may be performed using a system 300 as showed and described with reference to FIG. 3A, for example. In some embodiments, the method 100 may be used to fabricate or modify an implant for an animal or a human. Additionally, the method 100 may be used to fabricate or modify an implant (e.g., a cosmetic implant or a functional implant) of at least one of or a portion of at least one of a cranium, a neck, a spine, a shoulder, a knee, a rib cage, a leg, an arm, a hand, a foot, a wrist, an ankle, a hip, a tooth, a jaw, a cheek, a forehead, a nose, a breast, an ear, a buttocks, a thigh, a calf, a uterus, a bicep, a tricep, a forearm, a kidney, a liver, a lung, a heart, a blood vessel, a pancreas, a gallbladder, a stomach, a large intestine, a small intestine, a colon, a finger, a toe, a pelvis, a vertebra, a clavicle, an elbow, soft tissue, connective tissue, a muscle, fat, a ligament, a tendon, an organ, a liver, a rectum, an anus, bronchi, a urinary bladder, a urethra, a spleen, a brain, a spinal cord, a testicle, a penis, an ovary, a mammary gland, a pituitary gland, an adrenal gland, a thyroid, a parathyroid, a prostate, skin, a tongue, an eye, a thymus, bone marrow, an intervertebral disc (e.g., annulus fibroses, nucleus populous), a craniofacial bone (e.g., a frontal, ethmoid, vomer, sphenoid, mandible, occipital, nasal, lacrimal, inferior nasal concha, maxiallary, zygomatic, temporal, palatine, parietal, malleus, incus, or stapes bone), a vertebral bone (e.g., a cervical, thoracic, lumbar, or sacral bone), a vertebral bone component (e.g., a vertebral body, pedicle, transverse process, mammillary process, lamina, spinous process, accessory process, vertebral foramen, superior articular process, inferior articular process, or articular facet for the sacrum), a rib (e.g., rib 1, rib 2, rib 3, rib 4, rib 5, rib 6, rib 7, rib 8, rib 9, rib 10, rib 11, or rib 12), a hyoid, a sternum, a first cervical vertebra (atlas), a C2 (axis) vertebra, a C3 vertebra, a C4 vertebra, a C5 vertebra, a C6 vertebra, a C7 vertebra, a thoracic vertebra (e.g., T1 vertebra, T2 vertebra, T3 vertebra, T4 vertebra, T5 vertebra, T6 vertebra, T7 vertebra, T8 vertebra, T9 vertebra, T10 vertebra, T11 vertebra, or T12 vertebra), a lumbar vertebra (e.g., L1 vertebra, L2 vertebra, L3 vertebra, L4 vertebra, or L5 vertebra), a sacrum, a coccyx, a bone of the upper extremity (e.g., a scapula, a clavicle, a humerus, a radius, an ulna, a scaphoid, a lunate, a triquetrum, a pisiform, a hamate, a capitate, a trapezoid, a trapezium, a metacarpal 1, a proximal phalange 1, a distal phalange 1, a metacarpal 2, a proximal phalange 2, a middle phalange 2, a distal phalange 2, a metacarpal 3, a proximal phalange 3, a middle phalange 3, a distal phalange 3, a metacarpal 4, a proximal phalange 4, a middle phalange 4, a distal phalange 4, a metacarpal 5, a proximal phalange 5, a middle phalange 5, or a distal phalange 5), a bone of the lower extremity (e.g., a hip, (such as an ilium, an ischium, or a pubis), a femur, a patella, a tibia, a fibula, a talus, a calcaneus, a navicular, a medial cuneiform, a middle cuneiform, a lateral cuneiform, a cuboid, a metatarsal 1, a proximal phalange 1, a distal phalange 1, a metatarsal 2, a proximal phalange 2, a middle phalange 2, a distal phalange 2, a metatarsal 3, a proximal phalange 3, a middle phalange 3, a distal phalange 3, a metatarsal 4, a proximal phalange 4, a middle phalange 4, a distal phalange 4, a metatarsal 5, a proximal phalange 5, a middle phalange 5, or a distal phalange 5). It is understood that other types of implants are also possible.

At block 102, the method 100 may include registering a plurality of intraoperative locations of a surgically resected anatomical region of a patient.

At block 104, the method 100 may include generating, based on the registered plurality of intraoperative locations, a two-dimensional representation of the registered plurality of intraoperative locations.

At block 106, the method 100 may include determining, based on the two-dimensional representation, a two-dimensional shape of an anatomical feature excised from the surgically resected anatomical region.

At block 108, the method 100 may include determining, based on the two-dimensional shape of the anatomical feature and a three-dimensional model of a portion of the patient that contains the surgically resected anatomical region, a three-dimensional shape of the anatomical feature.

At block 110, the method 100 may include fabricating or modifying an implant based on the three-dimensional shape of the anatomical feature.

The above-listed steps of the method 100 are described in further detail and alternate embodiments are provided with reference to the following figures.

Figure 2A:
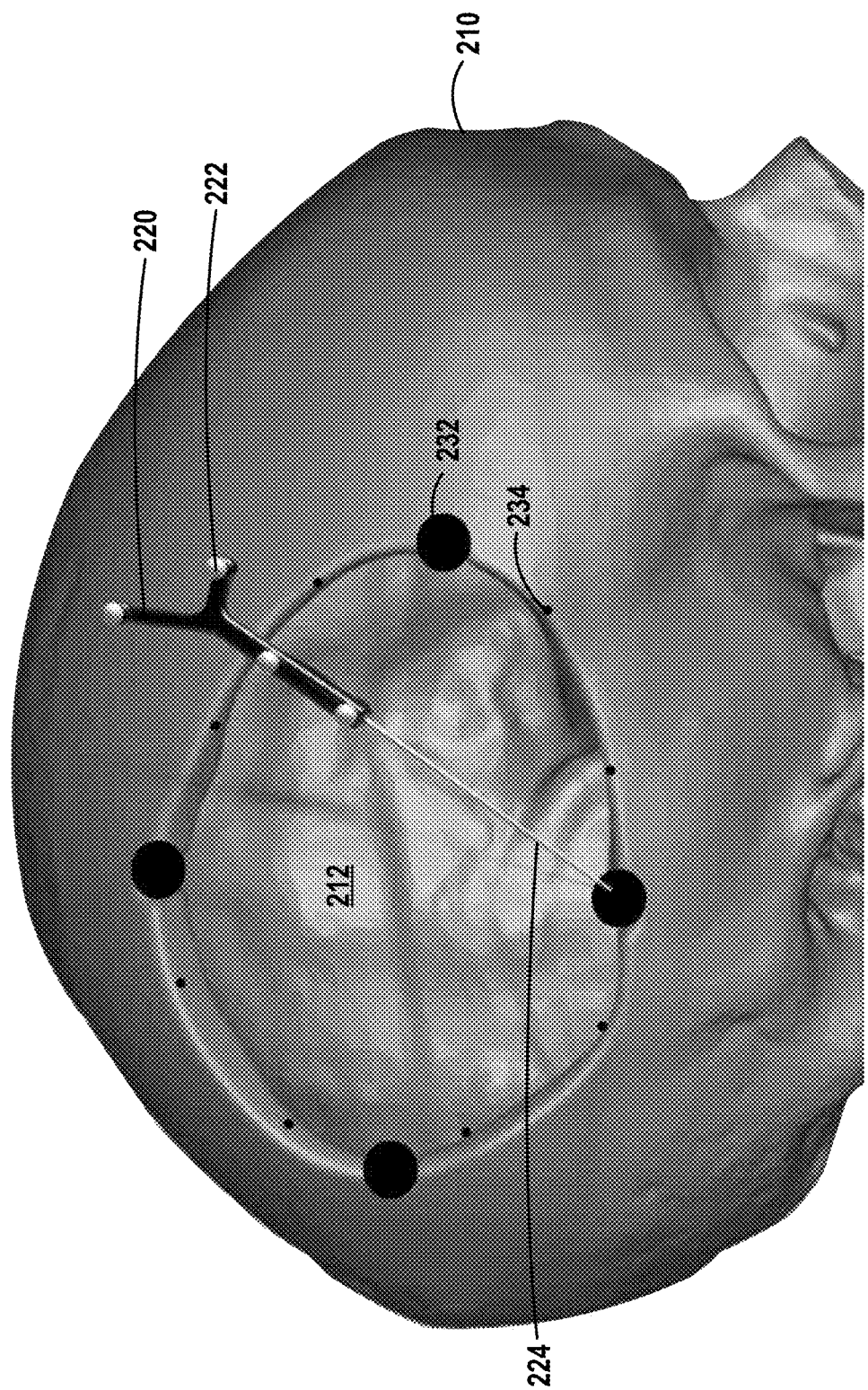
FIG. 2A is an illustration of a registration of a plurality of intraoperative locations of a surgically resected anatomical region of a patient, according to example embodiments.

FIG. 2A illustrates a process of registering a plurality of intraoperative locations of a surgically resected anatomical region 212 of a patient. As such, FIG. 2A may illustrate a portion of block 102 of the method 100. In the embodiment of FIG. 2A, the surgically resected anatomical region 212 of the patient may be a portion of the patient's cranium 210. It is understood that, in other embodiments, other biological substrates rather than a cranium may be used (e.g., in other embodiments, a maxillofacial portion of a patient may be the surgically resected anatomical region). An intraoperative probe 220 may be configured to register a plurality of the intraoperative locations of a surgically resected anatomical region of the patient. For example, as illustrated in FIG. 2A, the intraoperative probe 220 may be used to record the 3D coordinates of one or more of the intraoperative locations. In some embodiments, the intraoperative locations may include burr holes 232 and locations along cut lines 234 between adjacent burr holes 232. Additionally or alternatively, the intraoperative locations may include at least one boney feature (e.g., a process, a condyle, a facet, a head, a ramus, a crest, a epicondyle, a linea, a spine, a trochanter, a tubercle, a tuberosity, a fissure, a fontanel, a foramen, a fossa, a fovea, a meatus, a sinus, or a sulcus), muscular landmark (e.g., a muscular junction, a muscular feature, a muscular shape, or a muscular attachment to other parts of an anatomy), or an organ placement feature (e.g., vasculature, connective tissue, named ligaments, named structures, or contextual arrangement of organs). It is understood that other types of intraoperative locations are also possible.

The burr holes 232 may have been drilled into the surgically resected anatomical region 212 (e.g., using a bone drill). The radii of the burr holes 232 may be the same as one another or different from one another, in various embodiments. For example, in some embodiments, the burr holes 232 may each be about 4.4 mm in radius. The cut lines between adjacent burr holes 232 may represent locations at which a surgeon cut away a portion of the surgically resected anatomical region 212 (e.g., using a circulating saw, a scalpel, a bone saw, a dissecting knife, a lancet, an osteotome, a laser scalpel, and/or scissors) in order to remove the surgically resected anatomical region 212.

The intraoperative probe 220 may include an optical tracker and/or a magnetic tracker, for example. As such, the intraoperative probe 220 may be configured to capture or emit light, may include trackable fiducials (e.g., including reflective elements). In embodiments with a magnetic tracker, the intraoperative probe 220 may include a magnetic field generator and/or a passive coil in which a current is induced by a magnetic field produced by the magnetic field generator. Such a magnetic tracker can enable a detector of six degrees of freedom of the intraoperative probe 220. In various embodiments, for example, the intraoperative probe 220 may include an ultrasound probe; a 3D scanner; a multidimensional infrared probe; the NDI POLARIS from Northern Digital, Inc.; the NDI AURORA from Northern Digital, Inc.; or one or more of the devices described in U.S. Patent Application Publication Number 2008/0269588. Additionally or alternatively, in some embodiments, the intraoperative probe 220 may include one or more non-optical and non-magnetic trackers (e.g., a ruler, a depth gauge, calipers, a level, etc.). It is understood that other types of intraoperative probes are also possible.

As illustrated, in some embodiments, the intraoperative probe 220 may include one or more orientation indicators 222. The orientation indicators 222 may be spherically shaped or substantially spherically shaped, in various embodiments. In some embodiments, as illustrated, the intraoperative probe 220 may include four orientation indicators 222. In other embodiments, the intraoperative probe 220 may include fewer or greater numbers of orientation indicators 222 (e.g., one, two, three, five, six, seven, eight, nine, ten, fifteen, twenty, etc.). In various embodiments, the orientation indicators 222 may be arranged in an array (e.g., a one-dimensional (1D) array, a 2D array, or a 3D array).

In some embodiments, the orientation indicators 222 may include retroreflectors, infrared emitters, light-emitting diodes (LEDs), laser diodes, and/or optical sensors. In some embodiments, orientation indicators 222 may be illuminated sequentially to indicate their 3D coordinates to a receiver, for example. In alternate embodiments, the orientation indicators 222 (e.g., retroreflectors) may reflect light (e.g., emitted by one or more emitters) used in determining the 3D coordinates of the orientation indicators 222.

The intraoperative probe 220 may also include a tip 224 that a surgeon can use to indicate intraoperative locations. For example, the surgeon can place the tip at a given location and, based on the locations of the orientation indicators 222, 3D coordinates of the tip can be discerned (e.g., based on the length of the tip and the position of the orientation indicators 222 relative to the tip). In various embodiments, the tip 224 can include a pin, a metal rod, or an elongated plastic member.

In alternate embodiments, other ways of recording the coordinates of intraoperative locations may be used. For example, a light detection and ranging (LIDAR) system could be used to evaluate the surgically resected anatomical region 212 and determine where the intraoperative locations are located. Similarly, an image of the cranium 210 captured by a camera (e.g., a digital camera) could be analyzed (e.g., using a computer-vision algorithm, such as a machine-learning algorithm, object-identification algorithm, and/or edge-detection algorithm) to determine where the intraoperative locations are within the image.

In some embodiments, rather than a single intraoperative probe 220 being used, multiple intraoperative probes could be used (e.g., simultaneously). In such embodiments, multiple intraoperative locations could be identified, recorded, and/or registered simultaneously. Additionally or alternatively, in some embodiments, the intraoperative probe(s) 220 may include multiple pins. The multiple pins, in conjunction with the orientation indicator 222, may allow multiple intraoperative locations to be identified simultaneously by a single intraoperative probe 220.

Figure 2B:
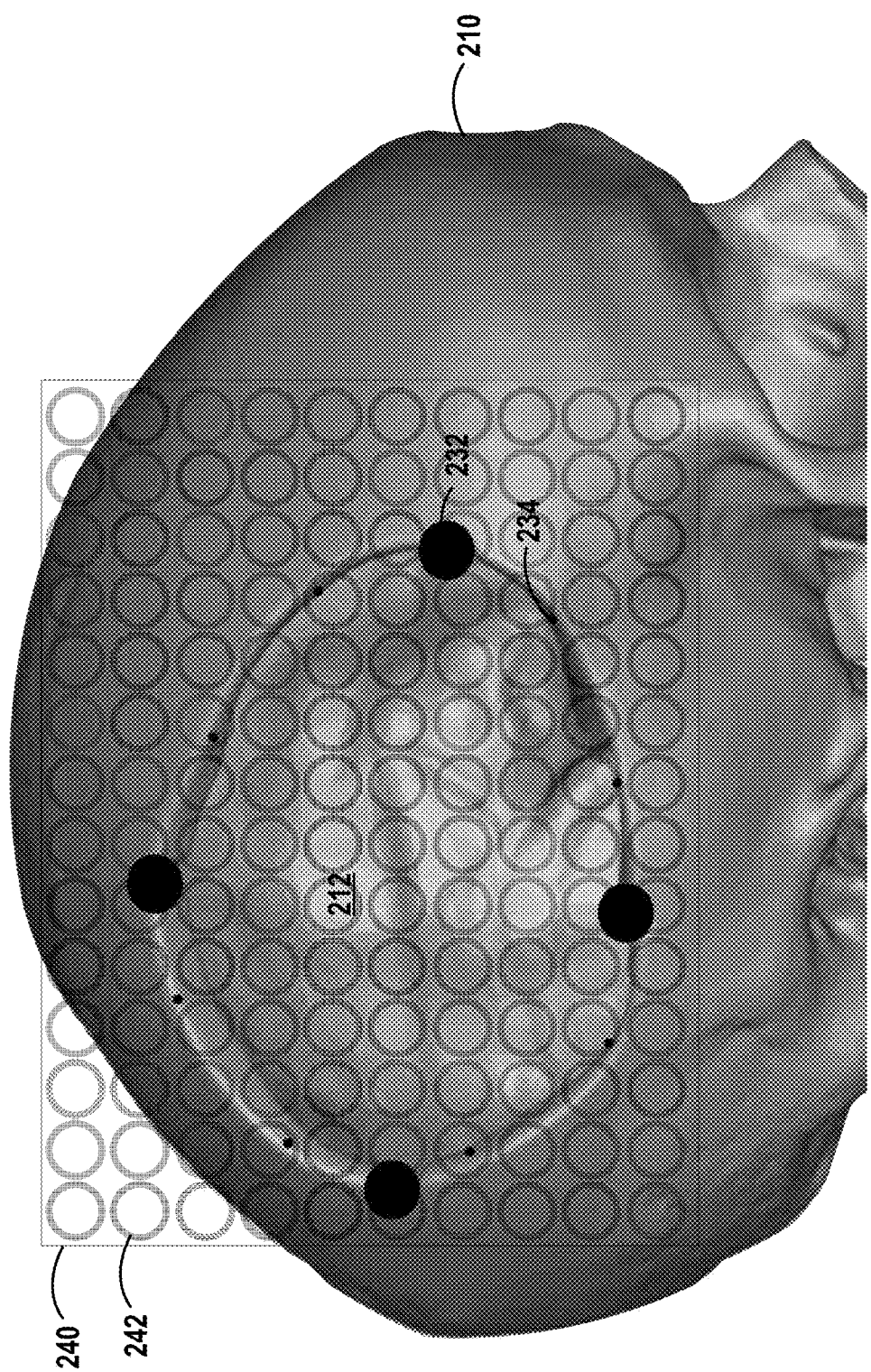
FIG. 2B is an illustration of a registration of a plurality of intraoperative locations of a surgically resected anatomical region of a patient, according to example embodiments.

In some embodiments, an array 240 of cameras 242 may be used to capture one or more images of the surgically resected anatomical region 212 of the patient. Such an embodiment is illustrated in FIG. 2B. As described above, a computer-vision algorithm (e.g., executed on a computing device), such as object identification and/or edge detection, could be used to register the burr holes 232 and/or the locations along cut lines 234 as intraoperative locations. For example, the edge of a bony region could be identified using an edge-detection algorithm. Using the identified edge of the bony region, locations along cut lines 234 could be identified in the image. Further, the separation (e.g., in horizontal and vertical directions) between the cameras 242 in the array 240, the angle of the array 240 relative to the patient, and/or the distance of the array 240 from the patient may be predetermined. Using such predetermined values, along with the separations between elements (e.g., intraoperative locations) within an image captured by the array 240 of cameras 242, absolute distances (e.g., distances between 3D coordinates) between multiple elements within the surgically resected anatomical region 212 may be determined.

Figure 2C:
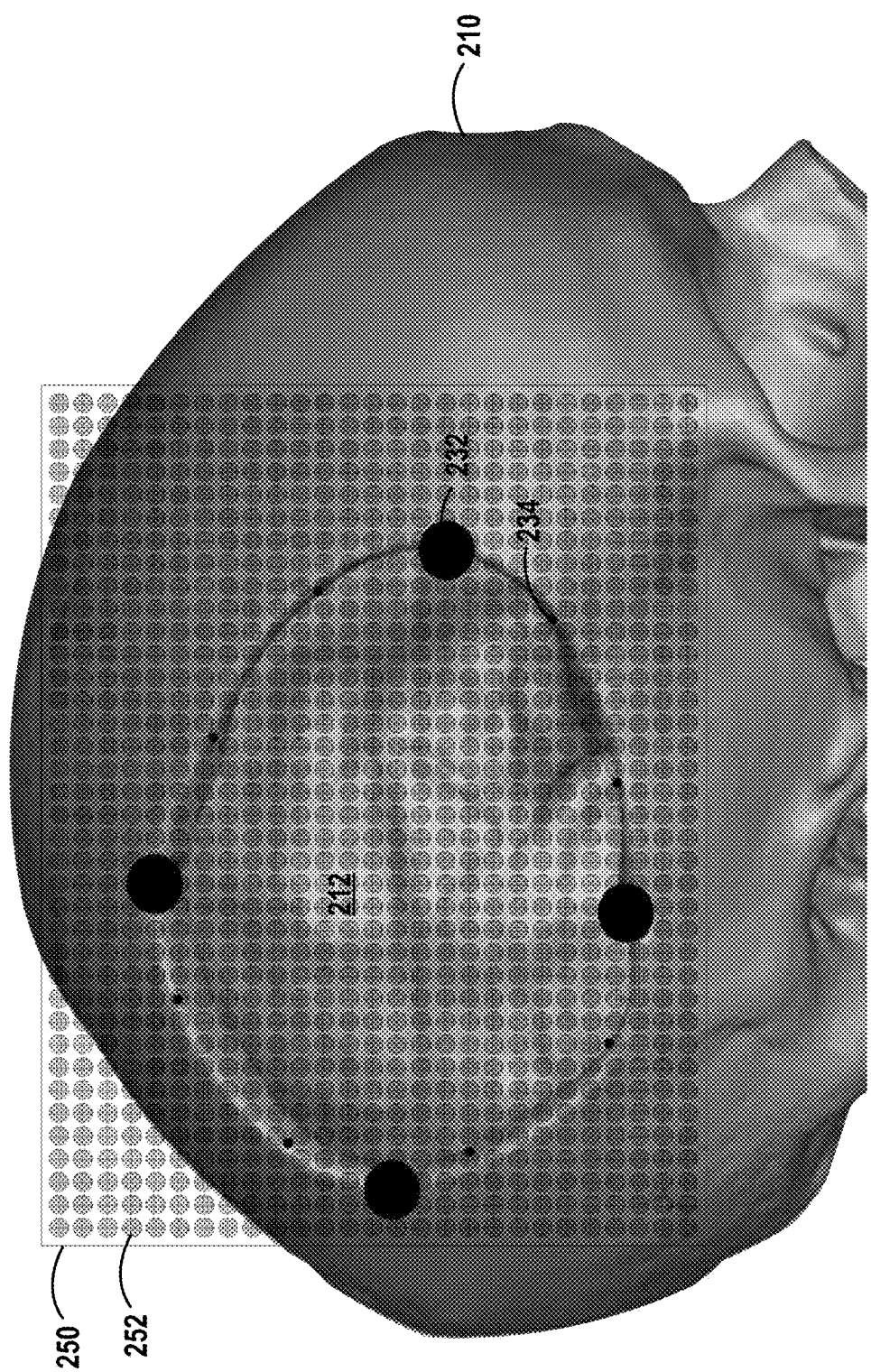
FIG. 2C is an illustration of a registration of a plurality of intraoperative locations of a surgically resected anatomical region of a patient, according to example embodiments.

In some embodiments, an array 250 of light emitters 252 may be used to project one or more features onto the surgically resected anatomical region 212 of the patient. Such an embodiment is illustrated in FIG. 2C. In some embodiments, the light emitters 252 may each include one or more white light sources. Alternatively, such light emitters 252 may project light in one or more wavelength ranges (e.g., within an infrared range, an optical range, an x-ray range, or any other range). For example, the light emitters 252 may each include one or more infrared (or other wavelength range) LEDs. Additionally or alternatively, such light may be filtered based on wavelength such that only a specific wavelength range is projected onto the surgically resected anatomical region 212. Similarly, such light may be passed through a polarization filter such that only a specific polarization or set of polarizations is projected onto the surgically resected anatomical region 212. In conditions (e.g., an operating room), where there may be additional extraneous sources of light which could impact the registration of intraoperative locations, the use of light having a predetermined polarization and/or light within a predetermined wavelength range may allow for the elimination of noise from a measurement due to light from sources that are not within the array 250, for example.

Figure 2D:
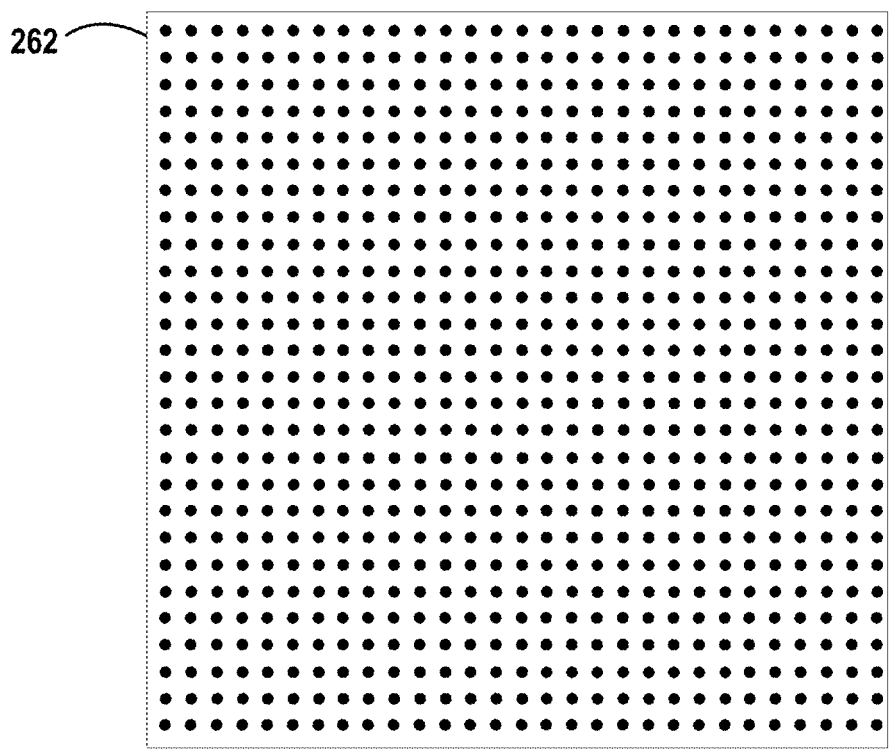
FIG. 2D is an illustration of a pattern projected onto a planar surface by an array of light emitters, according to example embodiments.
Figure 2E:
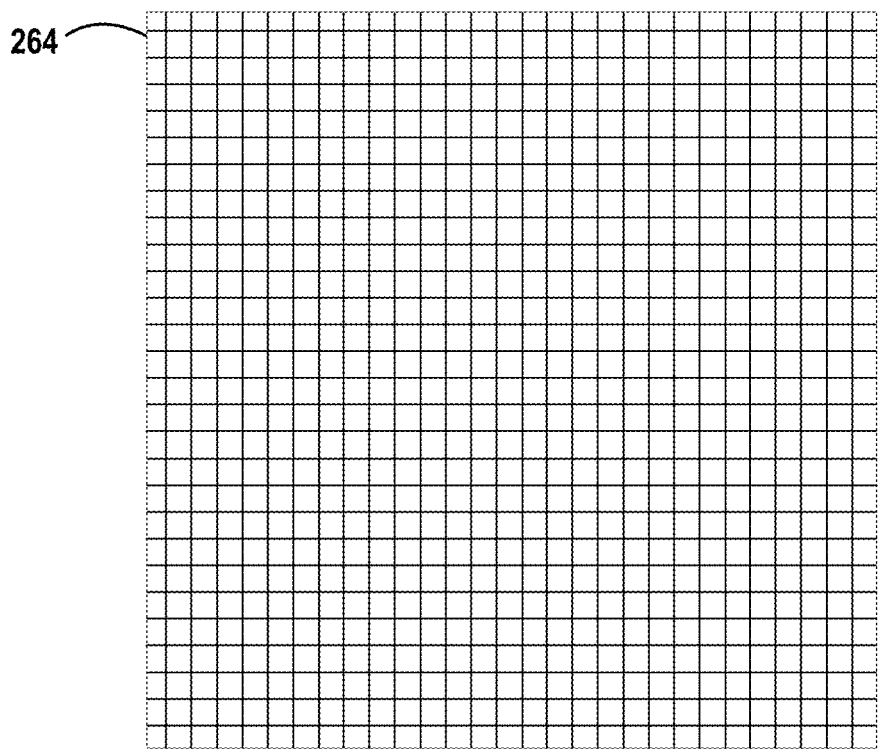
FIG. 2E is an illustration of a pattern projected onto a planar surface by an array of light emitters, according to example embodiments.

The features projected onto the surgically resected anatomical region 212 may be used to determine the locations and/or orientations of intraoperative locations (e.g., burr holes 232 and/or locations along cut lines 234). Examples of patterns that may be projected by the array 250 of light emitters 252 onto a planar surface are illustrated in FIGS. 2D and 2E. For example, an array of dots 262 (e.g., one dot per light emitter 252) may be projected onto a planar surface by the array 250 of light emitters 252. Alternatively, an array of lines 264 (e.g., an intersecting set of evenly spaced horizontal and vertical lines) may be projected onto a planar surface by the array 250 of light emitters 252.

By comparing the pattern projected onto a planar surface with the resulting pattern projected onto the surgically resected anatomical region 212 (e.g., as captured by one or more cameras, such as the array 240 of cameras 242 illustrated in FIG. 2B), intraoperative locations and/or a shape/size of the surgically resected anatomical region 212 may be determined.

Figure 2F:
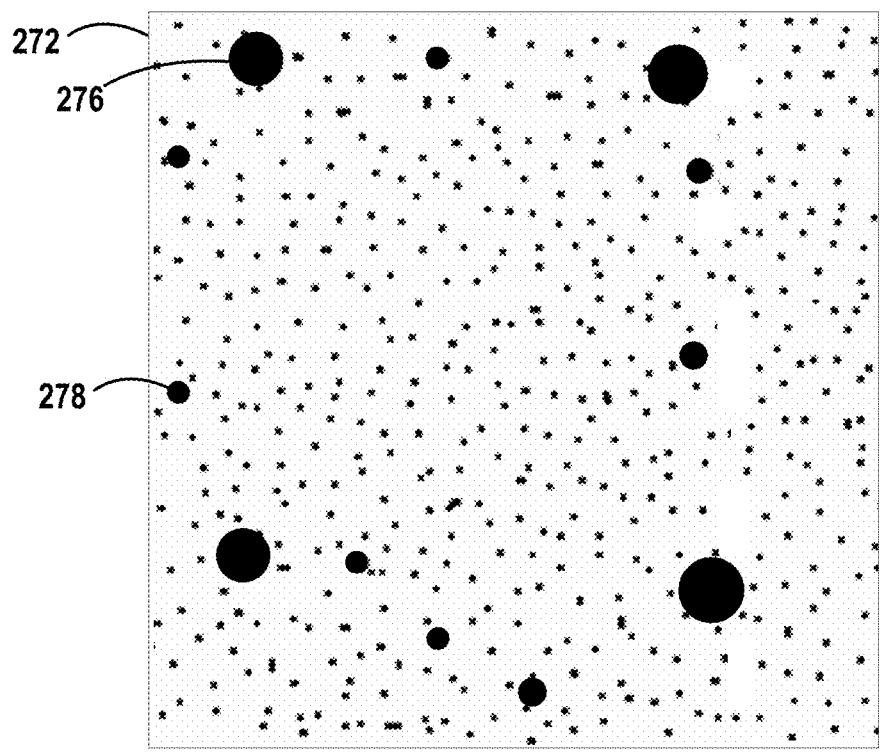
FIG. 2F is an illustration of a pattern projected onto a surgically resected anatomical region of a patient, according to example embodiments.

For example, an array of dots (e.g., the array of dots 262 illustrated in FIG. 2D) may appear differently when projected onto a surgically resected anatomical region 212. FIG. 2F illustrates a modified array of dots 272 based on a projection of light onto the surgically resected anatomical region 212 (e.g., projected onto the surgically resected anatomical region 212 by the array 250 of light emitters 252). The modified array of dots 272 may correspond to the array of dots 262 (e.g., projected onto the surgically resected anatomical region 212 rather than a planar surface). As illustrated in FIG. 2F, using the modified array of dots 272, locations of burr holes 276 and/or locations along cut lines 278 can be determined and/or registered. Such determinations and/or registrations of the locations of burr holes 276 and/or locations along cut lines 278 may be made based on the density of the dots in the array of dots 272 and/or one or more separations between dots in the array of dots 272 compared (e.g., respectively) to the density of the dots in the array of dots 262 when projected onto a planar surface and/or one or more separations between dots in the array of dots 262 when projected onto a planar surface.

Figure 2G:
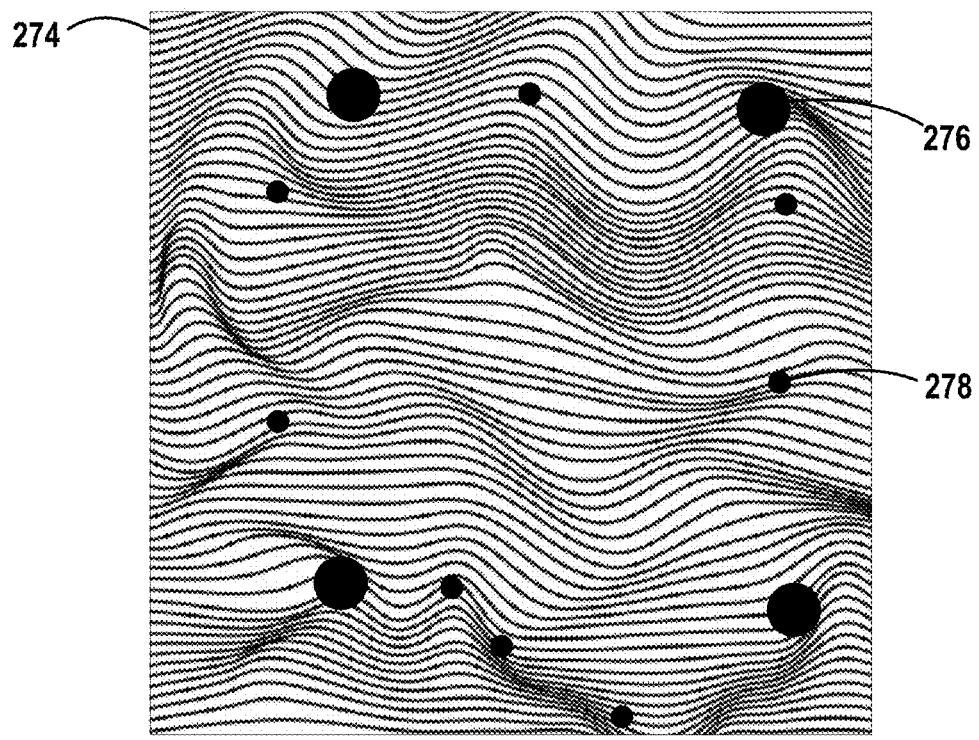
FIG. 2G is an illustration of a pattern projected onto a surgically resected anatomical region of a patient, according to example embodiments.

As another example, FIG. 2G illustrates a modified array of lines 274 based on a projection of light onto the surgically resected anatomical region 212 (e.g., projected onto the surgically resected anatomical region 212 by the array 250 of light emitters 252). The modified array of lines 274 may correspond to the array of lines 264 (e.g., projected onto the surgically resected anatomical region 212 rather than a planar surface). As illustrated in FIG. 2G, using the modified array of lines 274, locations of burr holes 276 and/or locations along cut lines 278 can be determined and/or registered. Such determinations and/or registrations of the locations of burr holes 276 and/or locations along cut lines 278 may be made based on the density of the lines in the array of lines 274 and/or one or more separations between lines in the array of lines 274 compared (e.g., respectively) to the density of the lines in the array of lines 264 when projected onto a planar surface and/or one or more separations between lines in the array of lines 264 when projected onto a planar surface.

Figure 3A:
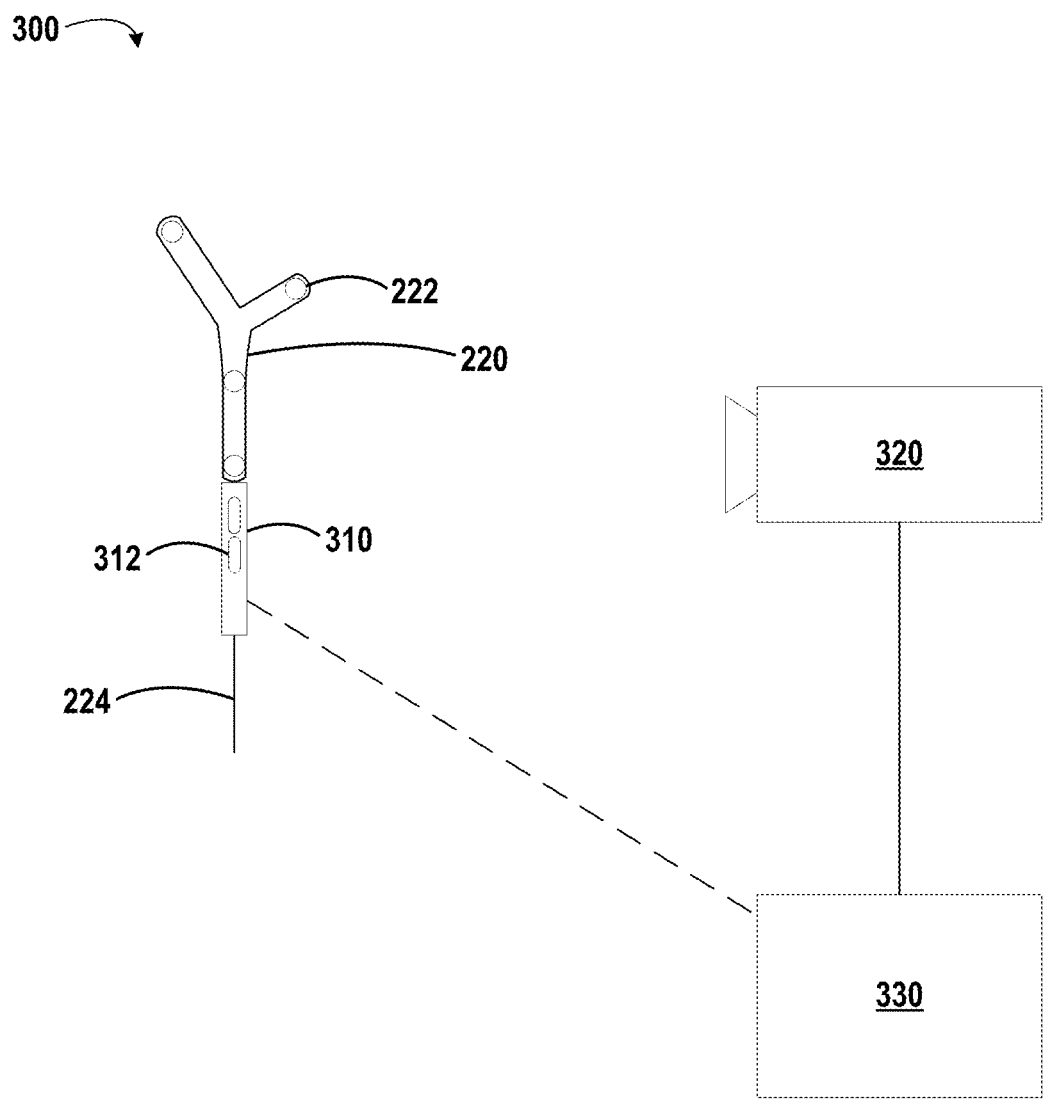
FIG. 3A is an illustration of a system, according to example embodiments.

FIG. 3A illustrates a system 300. The system 300 may be used to perform the method 100 of FIG. 1, for example. The system 300 may include the intraoperative probe 220 (which may include the orientation indicators 222 and the tip 224). In some embodiments, as illustrated, the intraoperative probe 220 may also include a transmitter 310 and one or more buttons 312. Further, the system 300 may include a receiver 320 and a computing device 330.

In some embodiments, the transmitter 310 may include one or more power sources. For example, the transmitter 310 may include a battery or a wired connection to a wall outlet. Alternatively, the transmitter 310 may receive power (e.g., in a wired manner or wirelessly) from the receiver 320 or the computing device 330 (e.g., through a universal serial bus (USB) connection). In some embodiments, the transmitter 310 may communicate with the computing device 330, as illustrated by the dashed line. The communication may occur wirelessly (e.g., over WiFi or BLUETOOTH) or over a wired connection (e.g., via Ethernet connection or USB connection). Additionally or alternatively, the transmitter 310 may communicate with the receiver 320. In still other embodiments (e.g., embodiments without buttons 312), the transmitter 310 may not be included (e.g., if communication does not occur between the transmitter 310 and the receiver 320 or the computing device 330). For example, the orientation indicators 222 may be retroreflectors that reflect light emitted by the receiver 320. In such embodiments, a transmitter 310 might not be necessary.

One or more of the buttons 312 may be used (e.g., by a surgeon) to indicate when an intraoperative location (e.g., an intraoperative location presently being touched by the tip 224) is to be registered (e.g., by the receiver 320 and/or the computing device 330). For example, the surgeon may depress one or more of the buttons 312 such that the transmitter 310 (e.g., via a command to a microcontroller onboard the intraoperative probe 220) transmits a signal to the receiver 320 and/or the computing device 330 indicating that the present 3D coordinates of the tip 224 are to be registered as an intraoperative location. The buttons may be mechanical buttons, mechanical switches, touch screen buttons, or electrical switches, in some embodiments. Other types of buttons are also possible.

Additionally or alternatively, in instances where the orientation indicators 222 include light emitters, depressing one or more of the buttons 312 may cause one, a subset, or all of the orientation indicators 222 to emit light (e.g., in a predetermined sequence of illuminations). Such an emission of light may be recorded by the receiver 320 to determine the present 3D coordinates of the orientation indicators 222.

In alternate embodiments, other ways of indicating when an intraoperative location is to be registered may be used (e.g., besides depression of a button on the intraoperative probe 220). For example, in some embodiments, audible commands (e.g., voice command using the phrase "register this location"), haptic commands, gesture commands (e.g., moving the intraoperative probe 220 up and down or side to side or rotating the intraoperative probe 220 about its axis), or visual commands (e.g., nodding or hand waving) may be provided to the intraoperative probe 220, the receiver 320, and/or the computing device 330 to indicate that an intraoperative location is to be registered. Any of the methods described herein that are used to indicate when an intraoperative location is to be registered may be performed by an assistant, a nurse, a surgeon, a robot, or a computing device executing software, in various embodiments. It is understood that other entities could likewise provide an indication that an intraoperative location is to be registered.

The receiver 320 may be configured to receive 3D coordinates of the orientation indicators 222 (e.g., 3D coordinates with associated time-stamps). This may include receiving light (e.g., optical light or infrared light) emitted from the orientation indicators 222 and determining the positions of the orientation indicators 222 relative to one another. Additionally or alternatively, determining the position of the 3D coordinates of the orientation indicators 222 may include transmitting light (e.g., optical light or infrared light) from the receiver 320, having the light reflect and/or refract from orientation indicators 222, and receiving a reflected/refracted light signal from one or more of the orientation indicators 222. Such light may be scanned across various regions of space at various times, for example. This may enable a determination of location based on the time a reflected signal is measured by the receiver 320.

Further, in some embodiments, the receiver 320 may include a background map. Such a map may be placed relative to a patient to define a patient-centric set of coordinates (e.g., defined by a sagittal plane, a transverse (i.e., axial) plane, and/or a coronal plane). The patient-centric set of coordinates could allow the receiver 320 to receive 3D coordinates of the orientation indicators 222 relative to the patient's body. In other embodiments, the 3D coordinates based on the orientation indicators 222 may be global coordinates (e.g., x, y, and z coordinates relative to a reference set of coordinates based on the location and orientation of the receiver 320).

The receiver 320 may also be configured to receive a trigger signal from the intraoperative probe 220 (e.g., in response to one or more of the buttons 312 being depressed). Upon receiving the trigger signal, the receiver 320 may record (e.g., simultaneously or sequentially) the 3D coordinates of the orientation indicators 222.

After determining the 3D coordinates of the orientation indicators 222, the receiver 320 may transmit these coordinates to the computing device 330 (e.g., wirelessly or using a wired connection) for further analysis. Alternatively, the receiver 320 may itself perform additional analysis (e.g., using computing device components internal to the receiver 320). For example, the receiver 320 may determine the 3D coordinates of the tip 224 based on the 3D coordinates of the orientation indicators 222 and a predefined length/orientation of the tip 224.

In alternate embodiments, the system 300 may not include an intraoperative probe 220 or a receiver 320. For example, the system may instead include a camera (e.g., a digital camera) connected to the computing device 330. The camera may capture an image of the patient (e.g., with a 2D or 3D patient map as a backdrop), which may then be transmitted to the computing device 330. The computing device 330 may then use a computer-vision algorithm (e.g., employing machine learning, object recognition, and/or edge detection) to identify each of a plurality of intraoperative locations within the captured image. In this way, the computing device 330 could determine the 3D coordinates of each of the intraoperative locations within the image without recording those intraoperative locations using an intraoperative probe. For example, an edge-detection algorithm may include determining termination points of bony defects around a periphery of the surgically resected anatomical region.

Recording the 3D coordinates of the orientation indicators 222 and/or determining the 3D coordinates of the tip 224 may be steps that are part of block 102 of method 100 (e.g., registering a plurality of intraoperative locations of a surgically resected anatomical region of a patient), for example. The computing device 330 may also be configured to generate a 2D representation of the registered plurality of intraoperative locations, determine a 2D shape of an anatomical feature excised from a surgically resected anatomical region, and determine a 3D shape of the anatomical feature.

The computing device 330 may perform a variety of functions, as described above. In various embodiments, the computing device 330 may include a desktop computing device, a laptop computing device, a server computing device, a tablet computing device (e.g., an IPAD from Apple, Inc. or a GALAXY TABLET from Samsung Electronics Co.), or a mobile computing device (e.g., an IPHONE from Apple, Inc. or a GALAXY smartphone from Samsung Electronics Co.). Further, in some embodiments, the computing device 330 may be located remotely from the intraoperative probe 220 and/or the receiver 320. For example, the computing device 330 may be a cloud server that communicates with the intraoperative probe 220 and/or the receiver 320 over the public Internet.

The computing device 330 may include various computing components to perform the various processes described herein. To that point, FIG. 3B depicts an example embodiment of computing device components (e.g., functional elements of a computing device) that may be included in the computing device 330.

The computing device 330 may include a processor 332, a memory 334, and an input/output unit 336, all of which may be coupled by a system bus 338 or a similar mechanism. The processor 332 may include one or more central processing units (CPUs), such as one or more general purpose processors and/or one or more dedicated processors (e.g., application specific integrated circuits (ASICs), digital signal processors (DSPs), etc.).

The memory 334, in turn, may comprise volatile and/or non-volatile data storage and can be integrated in whole or in part with the processor 332. The memory 334 may store program instructions, executable by the processor 332, and data that are manipulated by these instructions to carry out the various methods, processes, or functions described herein. Alternatively, these methods, processes, or operations can be defined by hardware, firmware, and/or any combination of hardware, firmware, and software. Therefore, the memory 334 may include a tangible, non-transitory, computer-readable medium, having stored thereon program instructions that, upon execution by one or more processors 332, cause the respective devices to carry out any of the methods, processes, or functions disclosed in this specification or the accompanying drawings. For example, the memory 334 may include a non-transitory, computer-readable medium having instructions stored therein, wherein the instructions, when executed by a process, comprise: receiving a registered plurality of intraoperative locations of a surgically resected anatomical region of a patient; generating, based on the registered plurality of intraoperative locations, a two-dimensional representation of the registered plurality of intraoperative locations; determining, based on the two-dimensional representation, a two-dimensional shape of an anatomical feature excised from the surgically resected anatomical region; determining, based on the two-dimensional shape of the anatomical feature and a three-dimensional model of a portion of the patient that contains the surgically resected anatomical region, a three-dimensional shape of the anatomical feature; and outputting the three-dimensional shape, wherein the three-dimensional shape is usable to fabricate or modify an implant such that the implant is implantable into the surgically resected anatomical region of the patient. The memory 334 may also be configured to store compressed and non-compressed sensor data (e.g., sensor data received from one or more intraoperative probes).

The input/output unit 336 may serve to configure, control, and/or display the operation of the processor 332. The input/output unit 336 may also provide output based on the operations performed by the processor 332. For example, the input/output unit 336 may include a network controller that communicates with a network controller of the receiver 320 (e.g., to retrieve sensor data). Such a communication may occur wirelessly (e.g., over WiFi, BLUETOOTH, etc.) or in a wired fashion (e.g., over an Ethernet connection, a USB connection, etc.). Additionally or alternatively, the input/output unit 336 may communicate with a network communications controller of a web server (e.g., a cloud server). For example, 3D models (e.g., CT data or MM data) may be stored on a web server. Such three-dimensional models may be stored within a database (e.g., a structured query language (SQL) database) within the cloud server. The database may require credentials (e.g., a username and/or password) in order to access the data stored within the database (e.g., the 3D models). In addition, in some embodiments, completed 3D shapes of previously fabricated or modified implants may be uploaded to the cloud server by the input/output unit 336 such that the 3D shapes of the previously fabricated or modified implants are accessible by other computing devices.

Figure 4A:
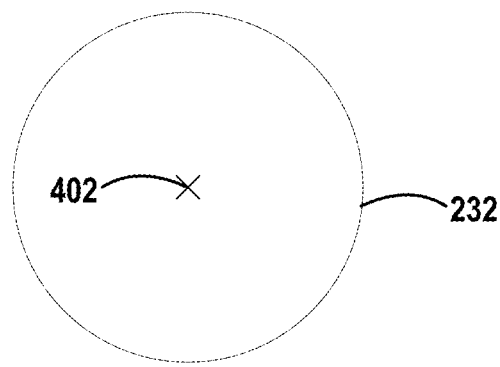
FIG. 4A is an illustration of a method of registering a burr hole, according to example embodiments.
Figure 4B:
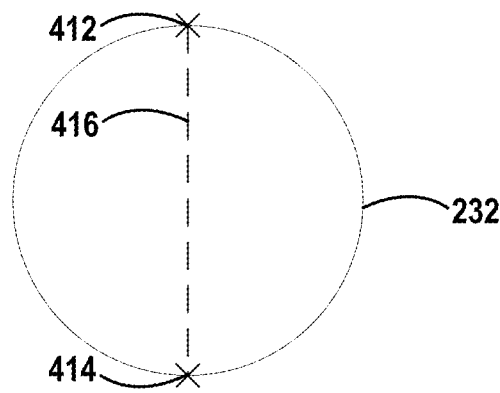
FIG. 4B is an illustration of a method of registering a burr hole, according to example embodiments.

FIGS. 4A and 4B illustrate two possible ways to register a burr hole (e.g., one of the burr holes 232 illustrated in FIG. 2A). The burr hole 232 may have been drilled during excision of a surgically resected anatomical region of a patient (e.g., during excision of a portion of a patient's cranium). Registering one or more burr holes 232 may be part of registering a plurality of intraoperative locations of a surgically resected anatomical region of a patient (e.g. block 102 of method 100), in some embodiments.

As illustrated in FIG. 4A, registering the burr hole 232 may include placing an intraoperative probe (e.g., a portion of the intraoperative probe 220 illustrated in FIG. 2A, such as the tip 224) at the burr hole 232 (e.g., at a center 402 of the burr hole 232). The burr hole 232 may be about 4.4 mm in radius, in some embodiments. Additionally or alternatively, the tip 224 of the intraoperative probe 220 may be between about 0.1 mm and about 1.0 mm in radius. After placing the intraoperative probe 220 at the burr hole 232, 3D coordinates of the intraoperative probe 220 (e.g., of the tip 224 of the intraoperative probe 220) may be transmitted to a computing device (e.g., the computing device 330 illustrated in FIG. 3A). In some embodiments, a receiver (e.g., the receiver 320 illustrated in FIG. 3A) may capture the 3D coordinates of the intraoperative probe 220 (e.g., of the tip 224 of the intraoperative probe 220) and then transmit those 3D coordinates to the computing device 330.

Alternatively, as illustrated in FIG. 4B, registering the burr hole 232 may include placing an intraoperative probe (e.g., a portion of the intraoperative probe 220 illustrated in FIG. 2A, such as the tip 224) at a first location 412 on a circumference of a circle corresponding to the burr hole 232. Registering the burr hole 232 may also include transmitting a first set of 3D coordinates of the intraoperative probe 220 (e.g., in response to depression of a button on the intraoperative probe 220) to a computing device (e.g., the computing device 330 illustrated in FIG. 3A). Further, registering the burr hole 232 may also include placing the intraoperative probe at a second location 414 on the circumference of the circle corresponding to the burr hole 232. In some embodiments, as illustrated in FIG. 4B, the second location 414 may be located on a diameter 416 of the circle corresponding to the burr hole 232 opposite the first location 412 (i.e., the second location 414 may be directly across the circle corresponding to the burr hole 232 from the first location 412). In addition, registering the burr hole 232 may include transmitting a second set of 3D coordinates of the intraoperative probe 220 (e.g., in response to depression of a button on the intraoperative probe 220) to the computing device (e.g., the computing device 330 illustrated in FIG. 3A). Thereafter, registering the burr hole 232 may include a computing device (e.g., the computing device 330 illustrated in FIG. 3A) determining a center of the circle corresponding to the burr hole 232.

In alternate embodiments, rather than sequentially transmitting two set of 3D coordinates to indicate a location of the burr hole 232, multiple intraoperative probes (e.g., two intraoperative probes) could be used. In such an embodiment, each of the intraoperative probes could be placed (e.g., each of the intraoperative probes' respective tips could be placed) at a different location on the circumference on the circle. Then, the 3D coordinates of each respective intraoperative probe could be simultaneously transmitted to the computing device 330 (e.g., through the receiver 320).

In still other embodiments, rather than transmitting discrete points along a circumference of the circle, one or more intraoperative probes could trace the circumference of the circle, transmitting sets of 3D coordinates during the trace (e.g., points every one, two, three, five, ten, fifteen, thirty, forty-five, sixty, ninety, one-hundred-and-twenty degrees, etc. around the circle). Then, based on these sets of 3D coordinates, the computing device could determine a center of the circle.

In yet other embodiments, rather than the computing device determining a center of the circle, the intraoperative probe and/or the receiver could determine a center of the circle corresponding to the burr hole 232 and only transmit the 3D coordinates of the center of the burr hole 232 to the computing device. For instance, the intraoperative probe could internally record the first location 412 and the second location 414. Then, the intraoperative probe could calculate (e.g., using an onboard microprocessor of the intraoperative probe) the center of the circle corresponding to the burr hole 232 based on the first location 412 and the second location 414 and transmit the result to the computing device. Additionally or alternatively, in a similar fashion, the receiver 320 could compute the center of the burr hole 232 and transmit the result to the computing device.

Figure 5A:
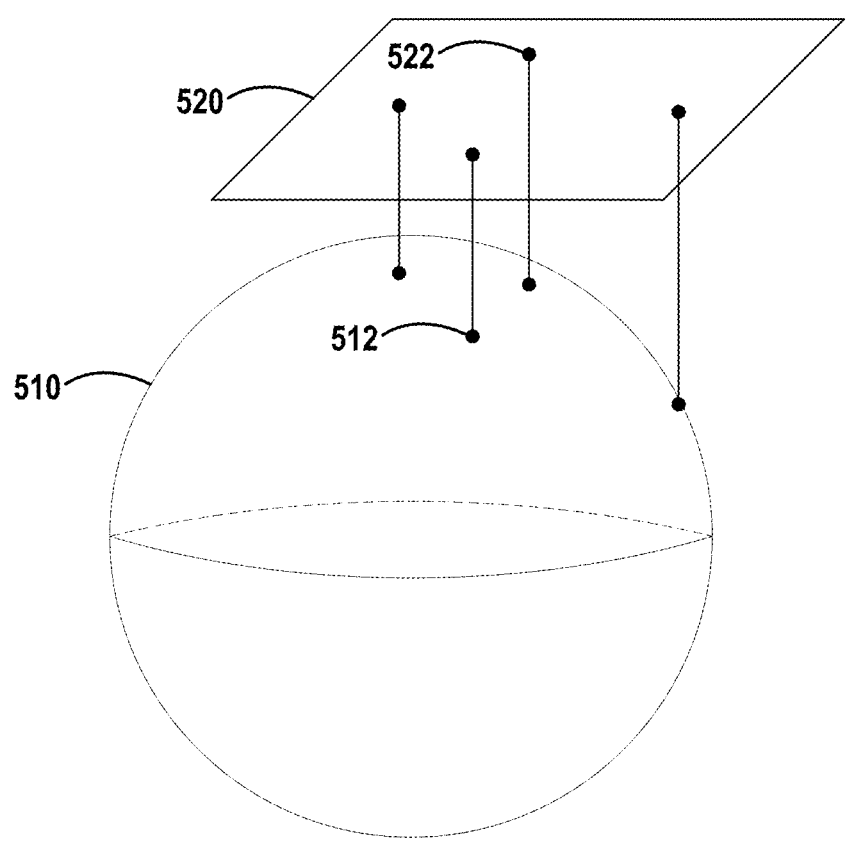
FIG. 5A is an illustration of a projection of three-dimensional intraoperative locations to generate a two-dimensional representation of the intraoperative locations, according to example embodiments.

FIG. 5A illustrates a process of projecting 3D intraoperative locations to generate a 2D representation of the intraoperative locations. Such a process may occur during block 104 of the method 100 (e.g., generating, based on the registered plurality of intraoperative locations, a 2D representation of the registered plurality of intraoperative locations), for example.

Reference numeral 510 is a spherical representation of the portion of the patient's body from which the surgically resected anatomical region was excised. It is understood that, in actuality, the patient's body (e.g., the patient's arm, cranium, leg, etc.) may not necessarily be spherical. As recorded (e.g., by the intraoperative probe), intraoperative locations 512 are located along the topography of the portion 510 of the patient's body. The intraoperative locations 512 may include registered burr holes and/or registered locations along cut lines, in various embodiments.

Figure 5B:
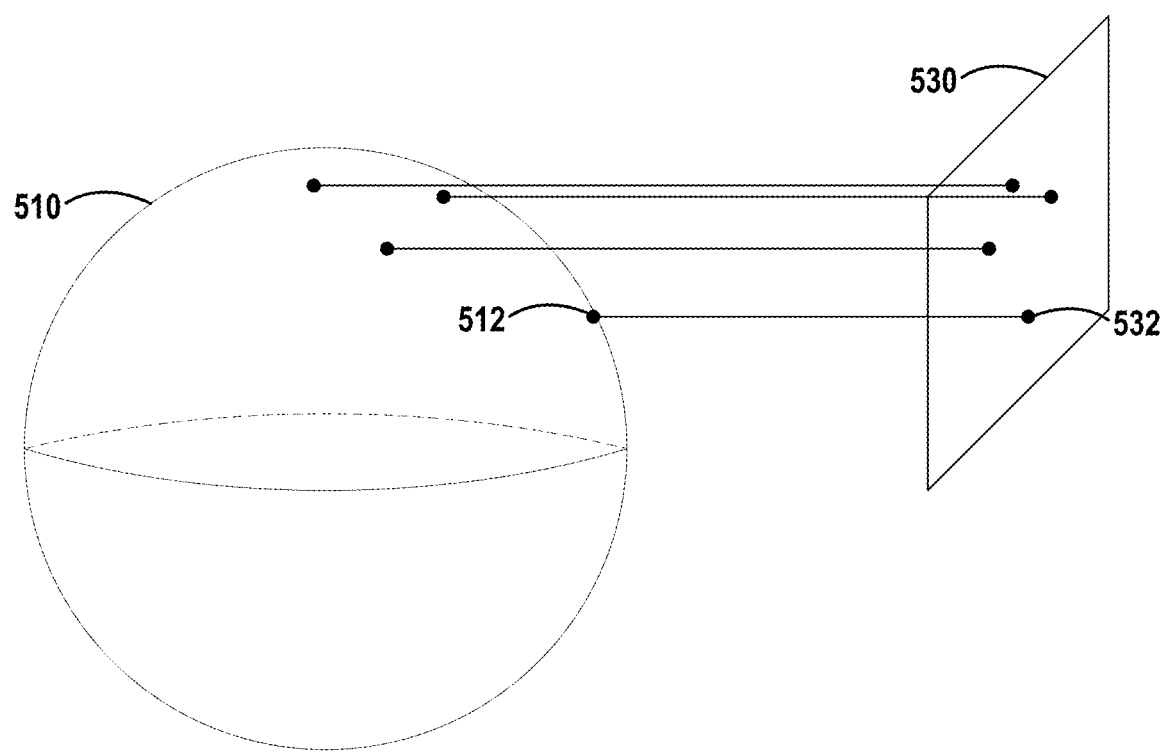
FIG. 5B is an illustration of a projection of three-dimensional intraoperative locations to generate a two-dimensional representation of the intraoperative locations, according to example embodiments.

The 3D intraoperative locations 512 may be projected onto a transverse plane 520 (i.e., axial plane) to generate projected intraoperative locations 522. The projected intraoperative locations 522 may be used to determine a 2D shape of an anatomical feature excised from the surgically resected anatomical region of the patient. In alternate embodiments, as illustrated in FIG. 5B, the 3D intraoperative locations 512 may instead be projected onto a sagittal plane 530 to generate projected intraoperative locations 532. In still other embodiments, the 3D intraoperative locations 512 could instead be projected onto a coronal plane (i.e., frontal plane). The 3D intraoperative locations 512 could be projected onto any two-dimensional plane. For example, the two-dimensional plane may be at angles with respect to the transverse plane, the sagittal plane, and/or the coronal plane. In some embodiments, for example, the plane onto which the 3D intraoperative locations 512 are projected may be determined (e.g., by the computing device), such that the aggregate of the distances, each calculated between each of the 3D intraoperative locations 512 and its corresponding 2D projected location on the perspective plane, is minimized.

Figure 6A:
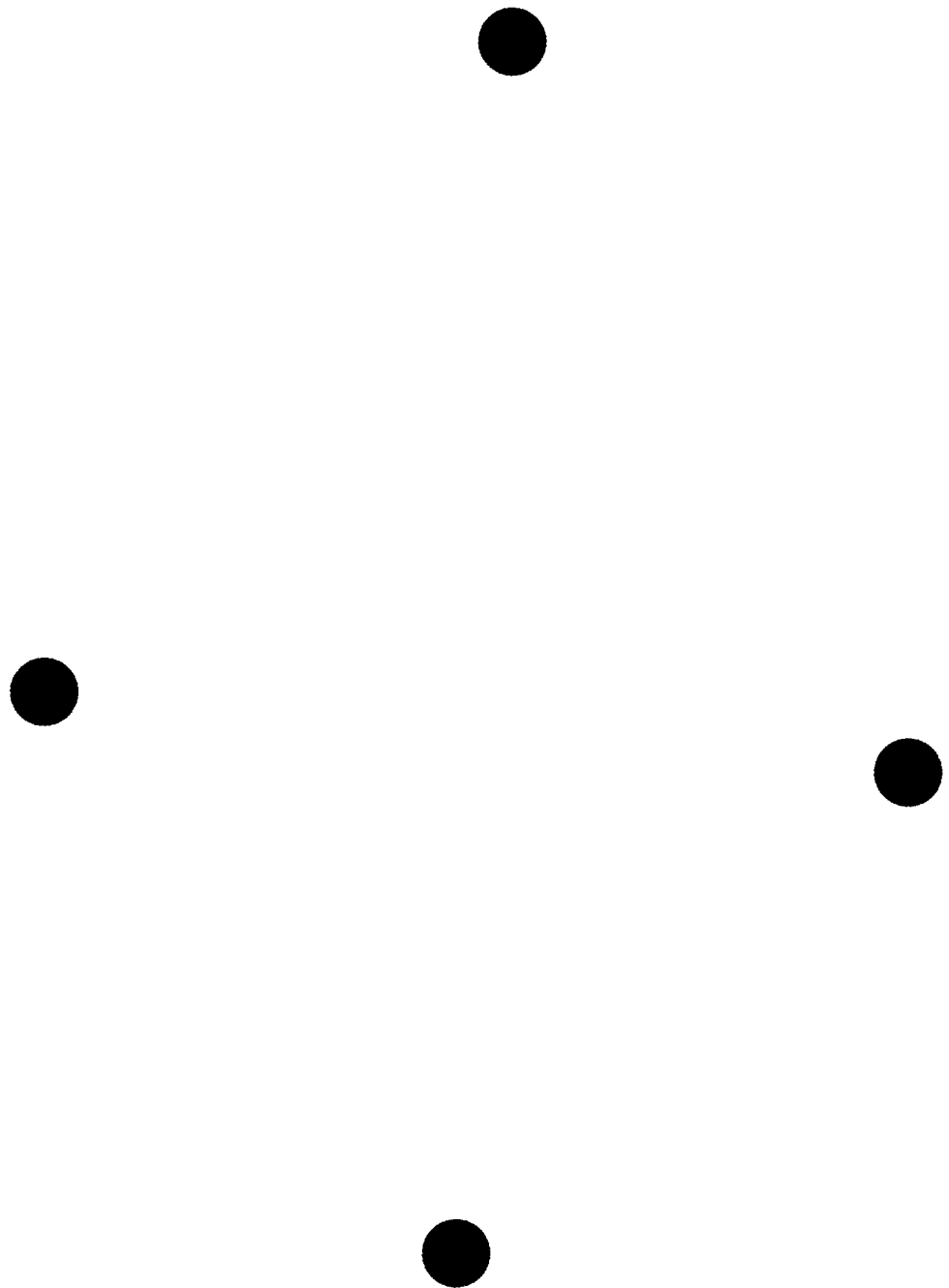
FIG. 6A is an illustration of a two-dimensional representation of intraoperative locations, according to example embodiments.

FIG. 6A illustrates a 2D representation of the intraoperative locations. The 2D representation may be generated during block 104 of the method 100 (e.g., generating, based on the registered plurality of intraoperative locations, a 2D representation of the registered plurality of intraoperative locations), for example. The projection of FIG. 6A may be the collection of the projected intraoperative locations 522 from FIG. 5A or the collection of the projected intraoperative locations 532 from FIG. 5B, for example. In other embodiments, the projection of FIG. 6A may represent a projection onto an intermediate plane (e.g., located three-dimensionally between the transverse plane 520, the sagittal plane 530, and the coronal plane).

Figure 6B:
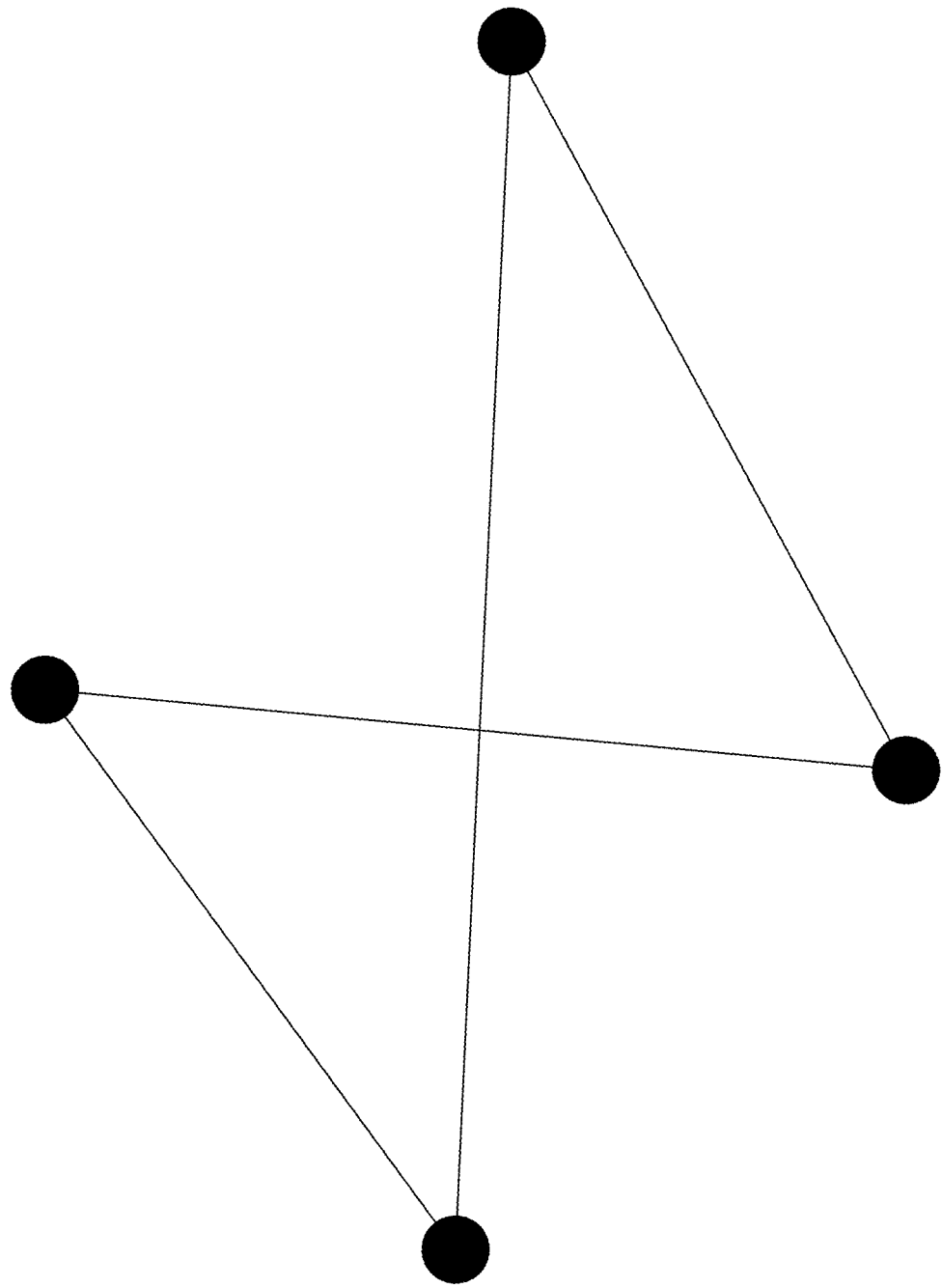
FIG. 6B is an illustration of a possible two-dimensional shape of an anatomical feature excised from a surgically resected anatomical region based on a two-dimensional representation of intraoperative locations, according to example embodiments.

Using the 2D representation of the registered plurality of intraoperative locations, a 2D shape of the anatomical feature can be determined (e.g., by the computing device 330). The 2D shape may be determined during block 106 of the method 100 (e.g., determining, based on the two-dimensional representation, a two-dimensional shape of an anatomical feature excised from the surgically resected anatomical region), for example. The 2D shape of the anatomical feature may be determined from a collection of possible shapes (e.g., polygons). Each of the possible shapes may be polygons that have as their vertices each of the registered plurality of intraoperative locations projected onto the 2D plane. Further, each of the possible shapes may be defined such that each of the projected intraoperative locations is included in the polygon. Each of the projected intraoperative locations may be connected to two other projected intraoperative locations, as illustrated in FIG. 6B. In embodiments having only two registered intraoperative locations, each of the projected intraoperative locations may be connected twice to the other intraoperative location. As illustrated, the polygons generated may be closed polygons. In some embodiments, only closed polygons may be considered as potential polygons that represent the 2D shape of the anatomical feature (e.g., non-closed polygons may be discarded from the collection of possible solutions).

Another possible polygon, formed using the projected intraoperative locations of FIG. 6A, is illustrated in FIG. 6C. Unlike the polygon of FIG. 6B, the polygon of FIG. 6B is not self-intersecting. In some embodiments, the requirement for non-self-intersecting may also be imposed on the potential polygons. As such, polygons that have edges that intersect with one another may be rejected. Additionally or alternatively, in some embodiments, a restriction may be imposed on the potential polygons that they be convex polygons (i.e., non-convex polygons may be discarded from the collection of possible solutions for the 2D shape of the anatomical feature).

As illustrated in both FIGS. 6B and 6C, linear interpolations may be used to connect the projected intraoperative locations to one another in order to define the polygon. Also as illustrated, the linear interpolations made between the projected intraoperative locations may be between centers of the intraoperative locations. In other embodiments, linear interpolations (or other types of interpolations) may be made between the outermost points of the projected intraoperative locations, the innermost points of the projected intraoperative locations, or some combination thereof.

Figure 6D:
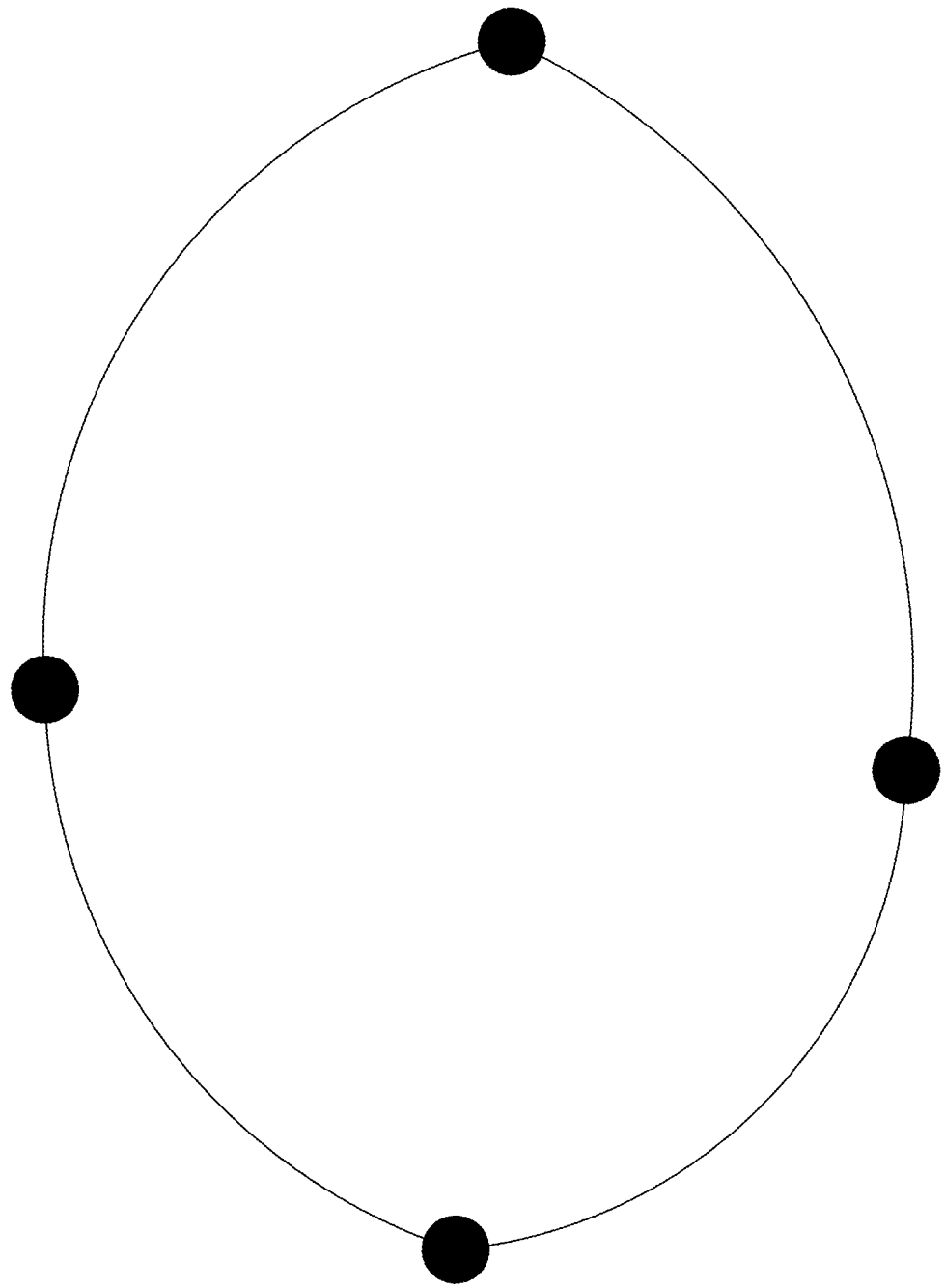
FIG. 6D is an illustration of a possible two-dimensional shape of an anatomical feature excised from a surgically resected anatomical region based on a two-dimensional representation of intraoperative locations, according to example embodiments.

Unlike the polygons illustrated in FIGS. 6B and 6C, in some embodiments, non-linear interpolations may be used between the projected intraoperative locations to produce a 2D shape. For example, as illustrated in FIG. 6D, curved interpolations (e.g., quadratic or exponential interpolations) could be made between projected intraoperative locations to produce a 2D shape. Other interpolation types are also possible, such as embodiments having multiple types of interpolations used within a single 2D shape. Further, in some embodiments, the computing device 330 may accept an input (e.g., from a surgeon) that indicates what type(s) of interpolations to use.

In FIGS. 6A-6D, the projected intraoperative locations may correspond to burr holes (e.g., the burr holes 232 illustrated in FIG. 2A). In order to further refine the determined 2D shape of the anatomical feature, additional intraoperative locations may be registered and projected onto the 2D plane. In some embodiments, this may include registering and projecting additional burr holes. As illustrated in FIG. 7A, in some embodiments, registering and projecting additional intraoperative locations may include registering and projecting one or more locations along cut lines (e.g., the locations along cut lines 234 illustrated in FIG. 2A). Additional projected intraoperative locations (e.g., locations along cut lines 234) may assist in defining the outer bounds of the 2D shape of the anatomical feature. The representation illustrated in FIG. 7A may be generated during block 104 of method 100 (e.g., generating, based on the registered plurality of intraoperative locations, a two-dimensional representation of the registered plurality of intraoperative locations), for example.

Figure 7B:
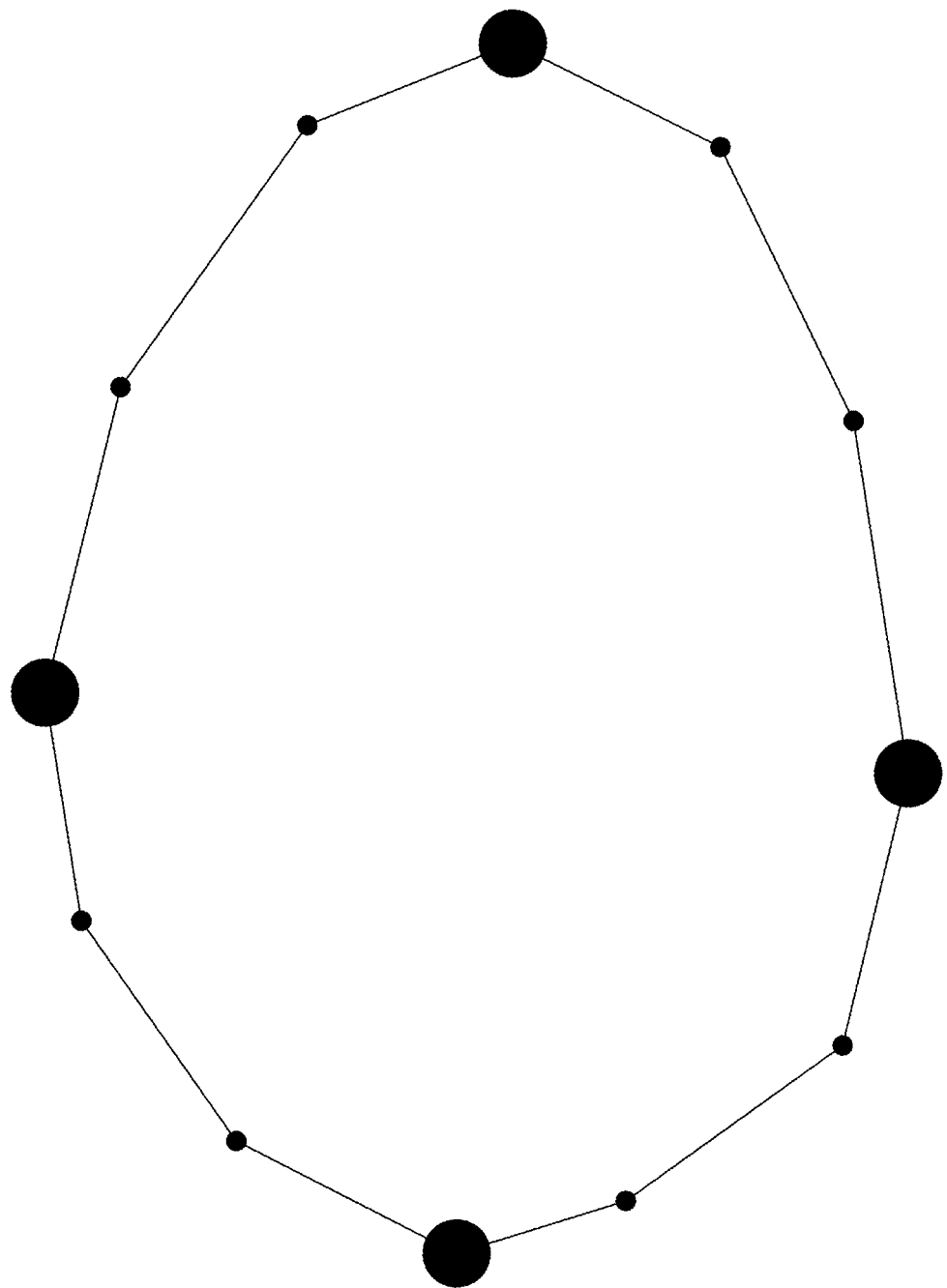
FIG. 7B is an illustration of a possible two-dimensional shape of an anatomical feature excised from a surgically resected anatomical region based on a two-dimensional representation of intraoperative locations, according to example embodiments.

FIG. 7B illustrates a linear interpolation between the projected intraoperative locations illustrated in FIG. 7A. The linear interpolation may correspond to a 2D shape of the anatomical feature. The 2D shape illustrated in FIG. 7B may be determined during block 106 of the method 100 (e.g., determining, based on the two-dimensional representation, a two-dimensional shape of an anatomical feature excised from the surgically resected anatomical region), for example. The algorithm used to generate the 2D shape of FIG. 7B may be analogous to the algorithm used to generate the 2D shape of FIG. 6C.

Figure 7C:
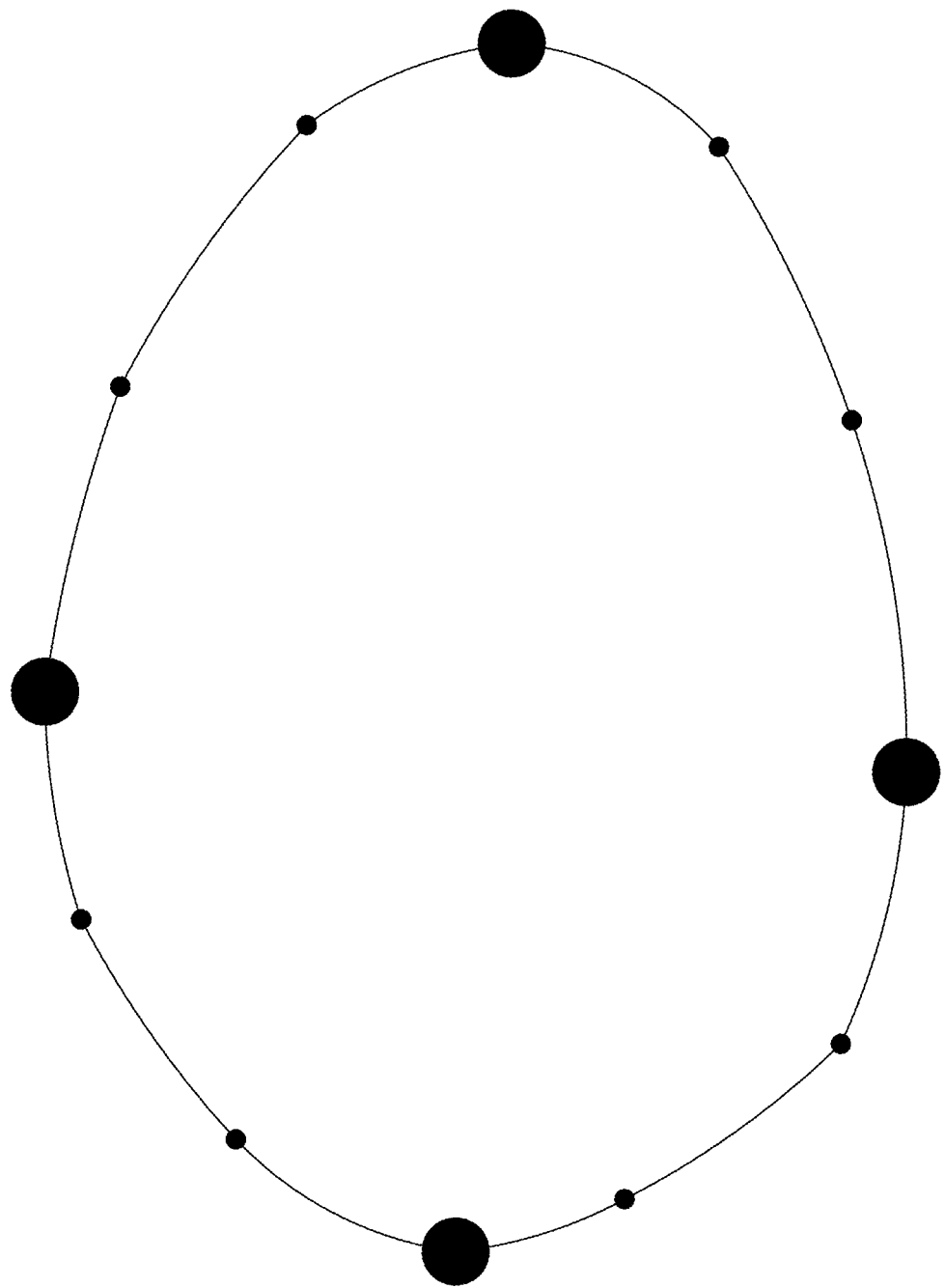
FIG. 7C is an illustration of a possible two-dimensional shape of an anatomical feature excised from a surgically resected anatomical region based on a two-dimensional representation of intraoperative locations, according to example embodiments.

FIG. 7C illustrates non-linear interpolations (e.g., quadratic or exponential interpolations) between the projected intraoperative locations illustrated in FIG. 7A. The non-linear interpolations may correspond to a 2D shape of the anatomical feature. The 2D shape illustrated in FIG. 7C may be determined during block 106 of the method 100 (e.g., determining, based on the two-dimensional representation, a two-dimensional shape of an anatomical feature excised from the surgically resected anatomical region), for example. The algorithm used to generate the 2D shape of FIG. 7C may be analogous to the algorithm used to generate the 2D shape of FIG. 6D.

As can be seen by comparing FIG. 7B to FIG. 6C and/or by comparing FIG. 7C to FIG. 6D, in some embodiments, the 2D shapes of FIGS. 7B and 7C may more accurately represent the 2D shape of the anatomical feature excised from the surgically resected anatomical region of the patient than the 2D shapes of FIGS. 6C and 6D. Likewise, resolutions (e.g., measured in vertices per 2D shape) of the 2D shapes of FIGS. 7B and 7C may be greater than the resolutions of the 2D shapes of FIGS. 6C and 6D.

If the resolution is high enough and/or the interpolation algorithm is sufficiently sophisticated, the resulting 2D shape of the anatomical feature could exactly mirror the actual projected 2D shape 702 of the anatomical feature excised from the surgically resected anatomical region of the patient. Such a resulting 2D shape is illustrated in FIG. 7D. For a determined 2D shape to approach the actual projected 2D shape 702 illustrated in FIG. 7, additional intraoperative locations (e.g., burr holes and/or locations along cut lines) can be registered (e.g., by a surgeon) in order to refine the resulting 2D shape.

Figure 8A:
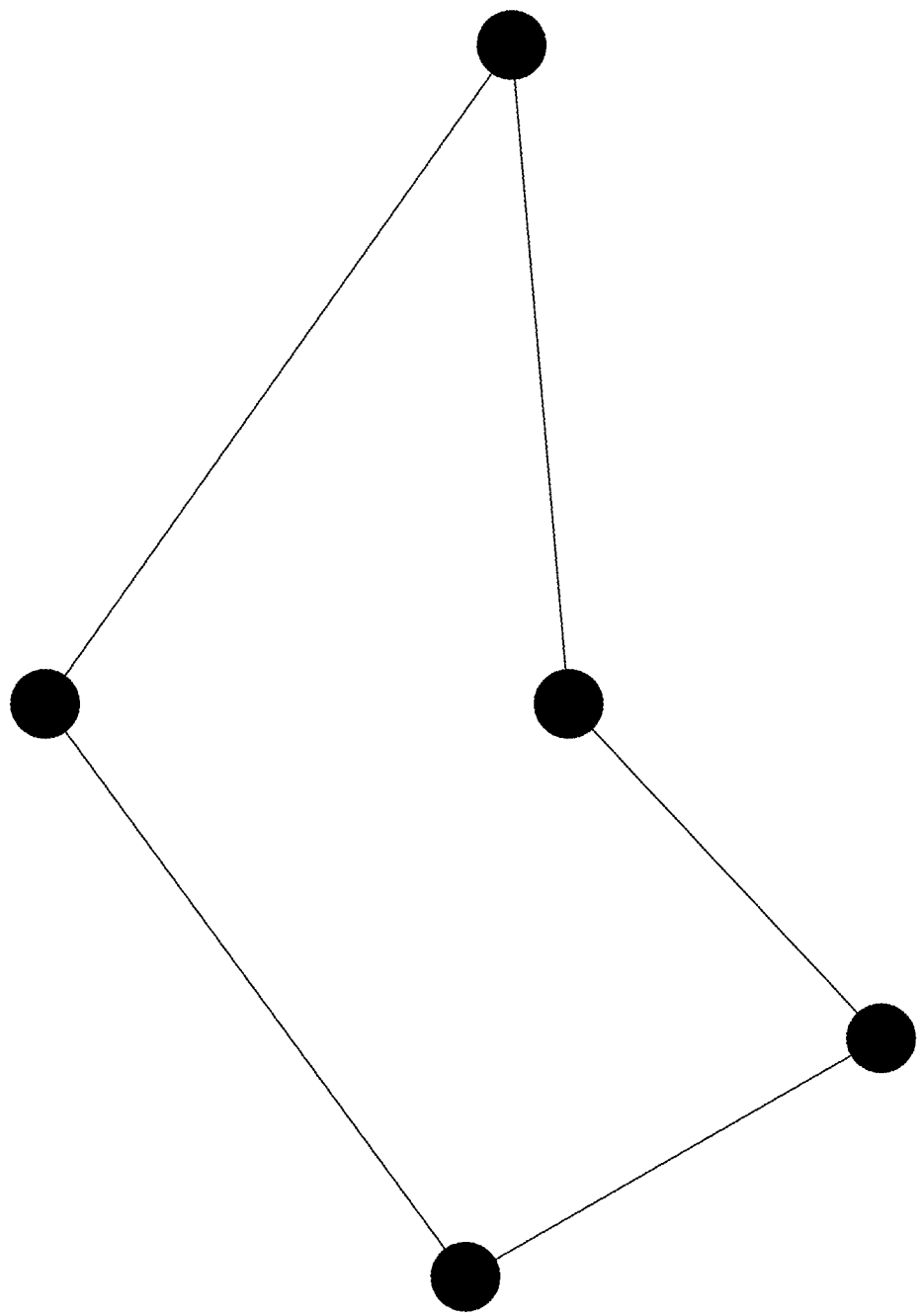
FIG. 8A is an illustration of a possible two-dimensional shape of an anatomical feature excised from a surgically resected anatomical region based on a two-dimensional representation of intraoperative locations, according to example embodiments.
Figure 8B:
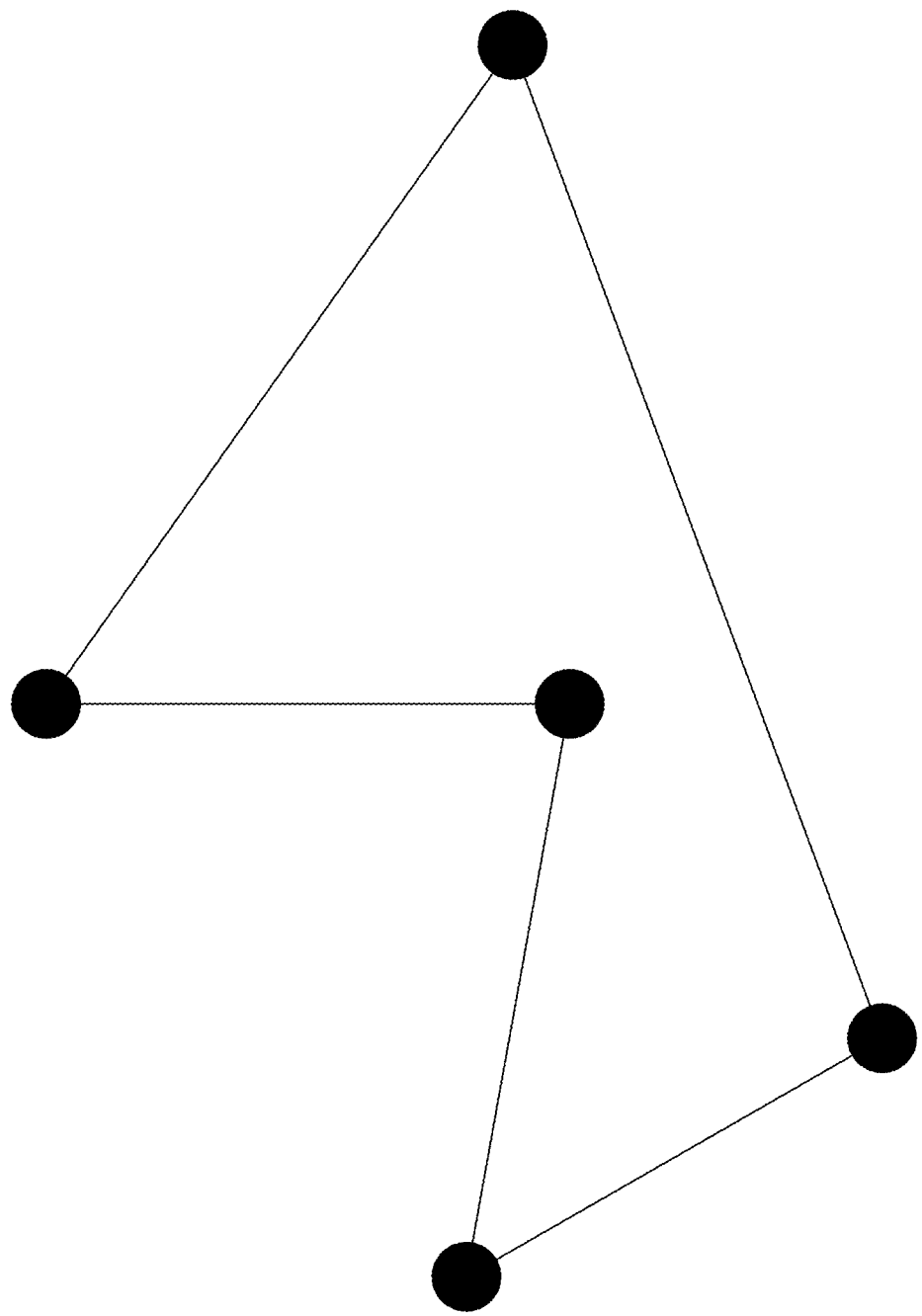
FIG. 8B is an illustration of a possible two-dimensional shape of an anatomical feature excised from a surgically resected anatomical region based on a two-dimensional representation of intraoperative locations, according to example embodiments.

In some embodiments, based on the 2D representation of the registered plurality of intraoperative locations, multiple possible corresponding 2D shapes of the anatomical feature that satisfy all the imposed restrictions may result. For example, if five intraoperative locations are projected onto a 2D plane to produce the 2D representation of FIGS. 8A and 8B, multiple possible 2D shapes may result. A first possible shape is illustrated in FIG. 8A and a second possible shape is illustrated in FIG. 8B. The shapes of FIGS. 8A and 8B may be determined during block 106 of method 100 (e.g., determining, based on the two-dimensional representation, a two-dimensional shape of an anatomical feature excised from a surgically resected anatomical region), for example. It is understood that the 2D shapes illustrated in FIGS. 8A and 8B are provided as examples, and other 2D shapes may be possible based on the 2D representation of the projected intraoperative locations.

As illustrated in FIGS. 8A and 8B, a linear interpolation between projected intraoperative locations may be used to define the respective 2D shapes. In alternate embodiments, alternate interpolation methods may be used. Also as illustrated, neither of the polygons corresponding to the 2D shapes of FIGS. 8A and 8B are convex polygons. In embodiments where the plurality of projected intraoperative locations cannot be interconnected to form a convex polygon while still including every intraoperative location as a vertex, a convex polygon requirement for the 2D shape may not be imposed. In still other embodiments, if a convex polygon cannot be formed by interconnecting vertices corresponding to each of the intraoperative locations, one or more of the projected intraoperative locations may be skipped (e.g., one or more of the projected intraoperative locations may be determined to be accidentally or inadvertently registered).

If multiple 2D shapes are produced that satisfy the imposed constraints, various methods (e.g., various algorithms executed by a processor of a computing device) may be used to determine which of the 2D shapes corresponds to the 2D shape of the anatomical feature excised from a surgically resected anatomical region. Any of the methods of making such a determination may be used during block 106 of method 100 (e.g., determining, based on the two-dimensional representation, a two-dimensional shape of an anatomical feature excised from the surgically resected anatomical region), for example.

Figure 8C:
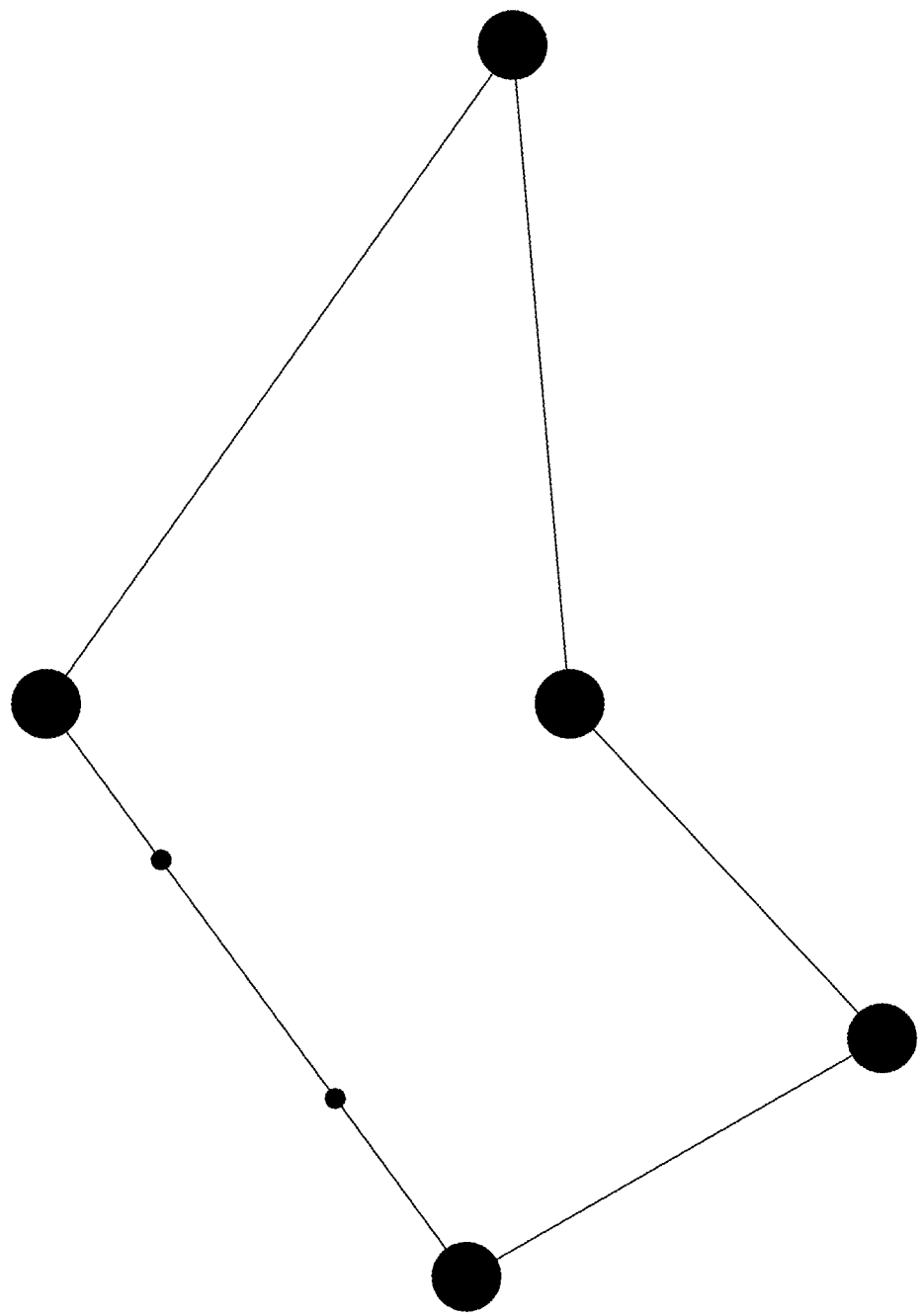
FIG. 8C is an illustration of a possible two-dimensional shape of an anatomical feature excised from a surgically resected anatomical region based on a two-dimensional representation of intraoperative locations, according to example embodiments.

In some embodiments, as illustrated in FIG. 8C, additional intraoperative locations may be registered and projected onto the 2D plane. Then, these additional intraoperative locations may be used to narrow down the number of possible 2D shapes. For example, if multiple 2D shapes are determined to be possible based on registered burr holes (e.g., corresponding to the burr holes 232 illustrated in FIG. 2A), locations along cut lines (e.g., the locations along cut lines 234 illustrated in FIG. 2A) may also be registered and projected onto the 2D plane. Then, based on the registered locations along cut lines, a list of possible 2D shapes may be refined by eliminating those 2D shapes that would not have cut lines corresponding to the registered locations along cut lines (e.g., the 2D shape of FIG. 8B would not have a cut line corresponding to the registered location along cut lines and is thus eliminated from being a possible 2D shape). In some embodiments, the locations along cut lines (or other intraoperative locations, such as additional burr holes), may be registered in response to an indication (e.g., to a surgeon) by a computing device (e.g., on a display) that multiple possible 2D shapes were determined and a request (e.g., to a surgeon) by the computing device (e.g., on a display) for registration of additional intraoperative locations to determine the proper 2D shape.

Additionally or alternatively, selecting the appropriate 2D shape may include projecting the determined 2D shapes onto one or more alternate 2D planes (e.g., the coronal plane rather than the sagittal plane, the transverse plane rather than the sagittal plane, etc.). Using the additional projection(s), improper 2D shapes may be eliminated from a list of possible 2D shapes.

In some embodiments, selecting the appropriate 2D shape may include displaying (e.g., by a computing device) each of the two or more possible polygons (e.g., possible closed polygons) that correspond to possible 2D shapes of the anatomical feature excised from the surgically resected anatomical region. Further, selecting the appropriate 2D shape may include receiving (e.g., by a computing device as an input from a surgeon) a selection of which of the two or more polygons (e.g., possible closed polygons) corresponds to the 2D shape of the anatomical feature. For example, a computing device may display all of the possible 2D shapes on a monitor and receive an input from a surgeon, a nurse, or an assistant (e.g., using a mouse and/or keyboard) that indicates which of the 2D shapes corresponds to the 2D shape of the anatomical feature. In some embodiments, rather than displaying the possible 2D shapes, the computing device may instead display what the resulting 3D shapes of the anatomical feature and/or 3D shapes of a resulting fabricated or modified implant would be that correspond to each 2D shape. Then, based on the corresponding 3D shapes of the anatomical features, a surgeon, a nurse, or an assistant may provide an input that indicates which of the 3D shapes corresponds to the anatomical feature. Based on this input, the proper 2D shape may be backed out (e.g., by a computing device). It is understood that the computing device may receive inputs from other sources besides surgeons, nurses, or assistants (e.g., from other computing devices or from a robot).

In still other embodiments, selecting the appropriate 2D shape may include comparing (e.g., by a computing device) each of the possible polygons (e.g., possible closed polygons) to previously determined 2D shapes of other anatomical features excised from other surgically resected anatomical regions. In such embodiments, selecting the appropriate 2D shape may also include determining (e.g., by a computing device) which of the two or more possible polygons (e.g., possible closed polygons) have a threshold probability of corresponding to the 2D shape of the anatomical feature excised from the surgically resected anatomical region.

In some embodiments, the other anatomical features excised from other surgically resected anatomical regions may correspond to additional anatomical features excised from one or more additional surgically resected anatomical regions of the patient. In the example of a cranioplasty, a surgeon may be presently removing/replacing a portion of the cranium on the right side of a patient's skull. In such an example, the one or more additional surgically resected anatomical regions of the patient may correspond to a different section of the cranium (e.g., on the left side of the patient's skull) that was previously resected by the surgeon (either during the present surgery or a previous surgery). Similarly, the one or more additional surgically resected anatomical regions of the patient may correspond to the arm, the chest, the leg, the hand, the foot, or any other anatomical region of a patient. In this way, if a surgeon has used a pattern for a patient before, it may be determined that such a pattern is more likely to have been used for the present resection. For example, if the surgeon cut a hexagonal shape for a previous cranioplasty on the left side of the patient's skull, the probability that a hexagonal shape was used may be higher than the probability that a square shape or an octagonal shape was used for the present cranioplasty on the right side of the patient's skull.

These probabilities may be computed (e.g., by a computing device) by comparing the prospective projected 2D shapes to previous projected 2D shapes for each of the one or more additional surgically resected anatomical regions of the patient. A threshold probability may be predefined by the computing device or by a user of the computing device. Those prospective projected 2D shapes that have a probability above the threshold may be retained as possible 2D shapes, while other 2D shapes may be removed from a list of possible 2D shapes. In some embodiments, rather than comparing the probabilities to a threshold probability, the 2D shape with the highest probability may be selected as the actual 2D shape that corresponds to the anatomical feature excised from the surgically resected anatomical region.

In other embodiments, the other anatomical features excised from the other surgically resected anatomical regions may correspond to similar anatomical features excised from one or more similar surgically resected anatomical regions of one or more other patients. In such a way, if a given surgeon, or if a collection of surgeons (either including a surgeon performing the present surgical procedure or not including the surgeon performing the present surgical procedure), tend to cut a certain pattern when resecting a given region of the body across multiple patients, this can be taken into account when determining the probability and/or when determining which 2D shape corresponds to the anatomical feature excised from the surgically resected anatomical region of the present patient. For example, if a given surgeon, or if a collection of surgeons (either including a surgeon performing the present surgical procedure or not), tend to cut square shapes when resecting portions of a cranium of any given patient, the 2D shape may be more likely to correspond to a square shape than to other shapes (e.g., square shapes have a higher probability of corresponding to the 2D shape of the excised anatomical feature than other shapes do). It is understood that this analogously applies to any biological substrate and is not specific to the cranium.

Once a projected 2D shape (e.g., the projected 2D shape 702 illustrated in FIG. 7D) corresponding to the 2D shape of the anatomical feature excised from the surgically resected anatomical region of the present patient is determined, the projected 2D shape may be used to determine a 3D shape of the anatomical feature. In some embodiments, the 3D shape of the anatomical feature may be determined by a computing device (e.g., the computing device 330 illustrated in FIG. 3A). Determining the 3D shape of the anatomical feature may be part of block 108 of method 100 (e.g., determining, based on the two-dimensional shape of the anatomical feature and a three-dimensional model of a portion of the patient that contains the surgically resected anatomical region, a three-dimensional shape of the anatomical feature), for example.

Figure 9A:
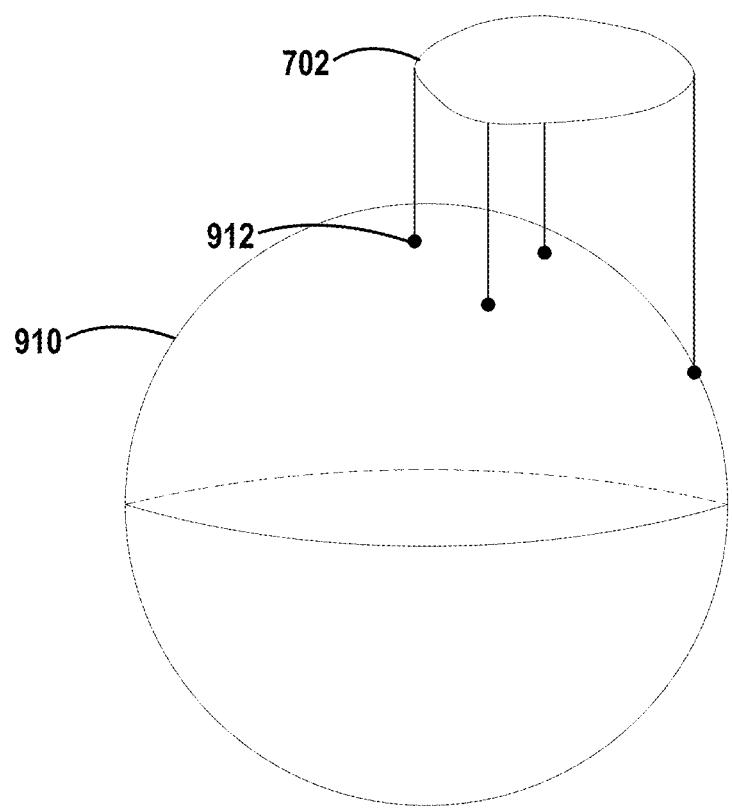
FIG. 9A is an illustration of a determination, based on a two-dimensional shape of an anatomical feature and a three-dimensional model of a portion of a patient that contains a surgically resected anatomical region, of a three-dimensional shape of the anatomical feature, according to example embodiments.
Figure 9B:
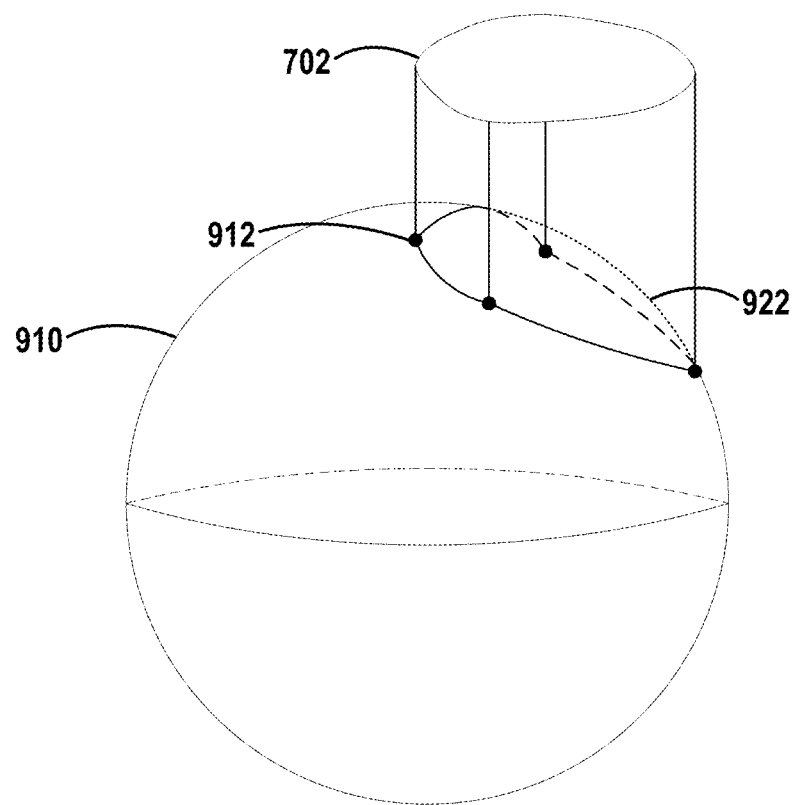
FIG. 9B is an illustration of a determination, based on a two-dimensional shape of an anatomical feature and a three-dimensional model of a portion of a patient that contains a surgically resected anatomical region, of a three-dimensional shape of the anatomical feature, according to example embodiments.
Figure 9C:
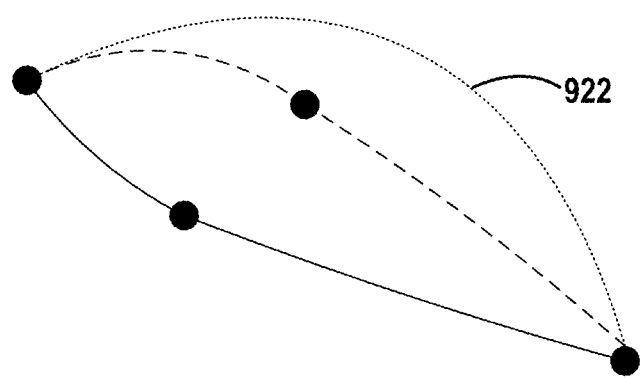
FIG. 9C is an illustration of a three-dimensional shape of an anatomical feature, according to example embodiments.

FIGS. 9A-9C illustrate a potential process of determining the 3D shape of the anatomical feature (e.g., based on the projected 2D shape 702 and a 3D model of a portion of the patient). As illustrated in FIG. 9A, the projected 2D shape 702 may be expanded to 3D by overlaying (i.e. "draping") the projected 2D shape 702 on the surface of a 3D model 910. The 3D model 910 may be a 3D model previously recorded of the patient (e.g., of the surgically resected anatomical region of the patient from which the anatomical feature was resected). For example, the 3D model 910 may include CT data and/or Mill data. Such CT data and/or Mill data may be recorded from a scan of the patient prior to the resection of the anatomical feature and/or subsequent to the resection of the anatomical feature. The 3D model 910 may correspond to a specific type of tissue (e.g., bone as defined within the CT data by a threshold Hounsfield unit (HU) reading, such as 100 HU, 250 HU, 500 HU, or 1000 HU). Alternatively, the 3D model 910 may include multiple types of tissue (e.g., both bone and muscle). It is understood that, in some embodiments, in addition to or instead of CT data and MRI data, other types of 3D models may be used.

In order to properly overlay the projected 2D shape 702 onto the 3D model 910, the projected 2D shape 702 may be oriented in relation to the 3D model 910 in correspondence with the 2D plane onto which it was projected. For example, as illustrated in FIG. 9A, the projected 2D shape 702 may be oriented on a transverse (i.e., axial) plane above the 3D model 910 before being overlaid onto the 3D model 910 because the projected 2D shape 702 was determined based on a plurality of intraoperative locations projected onto the transverse (i.e., axial) plane. In embodiments where the intraoperative locations were instead projected onto a sagittal plane, a coronal plane, and/or an intermediate plane, the projected 2D shape 702 may be overlaid onto the 3D model 910 from the appropriate corresponding plane (e.g., rather than the transverse plane). Reference numeral 912 is provided as an illustration of where the registered intraoperative locations 512 of FIG. 5A are positioned on the 3D model 910 after overlaying the projected 2D shape 702 on the 3D model 910.

FIG. 9B illustrates a 3D shape 922 of the anatomical feature based on the projected 2D shape 702 and the 3D model 910. The 3D shape 922 may correspond to the surface of the 3D model 910 that is bounded by the overlaid pattern from the projected 2D shape 702, for example.

In some embodiments, determining the 3D shape 922 of the anatomical feature may include performing (e.g., by a computing device) a volume element ("voxel") additive technique corresponding to regions of the 3D model 910 having a signal value above a threshold signal value that corresponds to bone. In some embodiments, within a region of a surface of the 3D model 910 bounded by the overlaid pattern from the projected 2D shape 702, there may be various biological materials. For example, in embodiments where a cranioplasty is being performed, there may be regions of bone, brain, and/or muscle, each encapsulated by the overlaid pattern from the projected 2D shape 702. In such embodiments, the implant to be fabricated or modified might only include some of the biological substrates encapsulated by the overlaid pattern (e.g., only bone or only bone and muscle). Hence, the 3D shape 922, which may subsequently be used to fabricate or modify the implant, might be defined based on only those regions of the 3D model 910 that correspond to bone.

The voxel-additive technique may include dividing the 3D model 910 up into various voxels. Each voxel may have an associated data value. For example, in embodiments where the 3D model 910 includes CT data, each voxel may include an associated data value that represents the Hounsfield unit (HU) value, the mean HU value, or the median HU value for all measured points within the voxel (e.g., measured during a CT scan of the surgically resected anatomical region). The voxel-additive technique may then include producing a list of those voxels that have an associated data value (e.g., an associated HU value) that is above or below a predefined threshold signal value (e.g., above a predefined threshold signal value that corresponds to bone, such as a predefined threshold signal value of 100 HU, 250 HU, 500 HU, or 1000 HU). Such a list of voxels may be used to define the 3D shape 922, for example. In this way, the 3D shape 922 can be made to only include those regions of a 3D model (e.g., the 3D model 910) that include a specific biological substrate.

In alternate embodiments, the 3D shape may include multiple biological substrates. In some embodiments, rather than defining a single threshold above or below which a region of the 3D model is included in the 3D shape, multiple regions may be defined within the 3D shape (e.g., based on signal value within the 3D model, such as an MRI signal value within the 3D model). For example, the 3D shape may include multiple layers of various biological substrates (e.g., a top layer corresponding to skin, a middle layer corresponding to muscle, and a bottom layer corresponding to bone) based on various threshold signal values or signal value ranges (e.g., a first signal value range corresponds to bone, a second signal value range corresponds to muscle, and a third signal value range corresponds to skin). In such embodiments, resulting implants can be fabricated or modified using a variety of materials of different densities to correspond to the various regions within the 3D shape that correspond to different biological substrates. As such, the resulting implant may mimic differing biological substrates of the anatomical feature excised from the surgically resected anatomical region. For example, one or more of those regions may include a material that mimics soft tissue (e.g., tendons, ligaments, skin, fat, fibrous tissues, muscles, nerves, blood vessels, etc.).

FIG. 9C illustrates a 3D shape 922 of an anatomical feature developed according to methods described herein (e.g., according to the process of overlaying the projected 2D shape 702 illustrated in FIGS. 9A and 9B). In FIG. 9C, the finely dashed line is intended to illustrate the three-dimensional curvature of a raised portion of the 3D shape 922 and the coarsely dashed line is intended to illustrate a hidden back edge of 3D shape 922. The 3D shape 922 may, in various embodiments, be convex or concave.

In some embodiments, the 3D shape 922 may correspond to a scaled version of the 3D shape of the anatomical feature. For example, in some embodiments, the projected 2D shape (e.g., the projected 2D shape 702 illustrated in FIGS. 9A and 9B) may be scaled by a scaling factor (e.g., between 0.99 and 1.0, between 0.95 and 0.99, between 0.90 and 0.95, between 0.85 and 0.90, between 0.80 and 0.85, between 0.75 and 0.80, or some other scaling factor) prior to overlaying the projected 2D shape 702 onto the 3D model 910. Thus, the resulting 3D shape 922 may also be scaled (e.g., shrunk). In this way, the 3D shape 922 may be a scaled version of the 3D shape of the anatomical feature.

In other embodiments, the 3D shape 922 may be determined using an unscaled projected 2D shape. However, after overlaying the projected 2D shape 702 onto the 3D model 910, the resulting 3D shape may be scaled to arrive at a final 3D shape. In this alternate fashion, the final 3D shape may be a scaled version of the 3D shape of the anatomical feature.

In still other embodiments, rather than scaling the entire 3D shape in any of the ways described above, an outer perimeter ("rim") of the 3D shape may be removed from the 3D shape while keeping the remaining features of the 3D shape the same size. Any of the methods described herein to reduce the overall size of the 3D shape may correspond to a smaller overall size of the implant. In other embodiments, the overall size of the 3D shape and the resulting implant may be increased or scaled up (e.g., using a scaling factor of between 1.0 and 1.01, between 1.01 and 1.05, between 1.05 and 1.10, between 1.10 and 1.15, between 1.15 and 1.20, between 1.20 and 1.25, or some other scaling factor), instead.

Figure 10A:
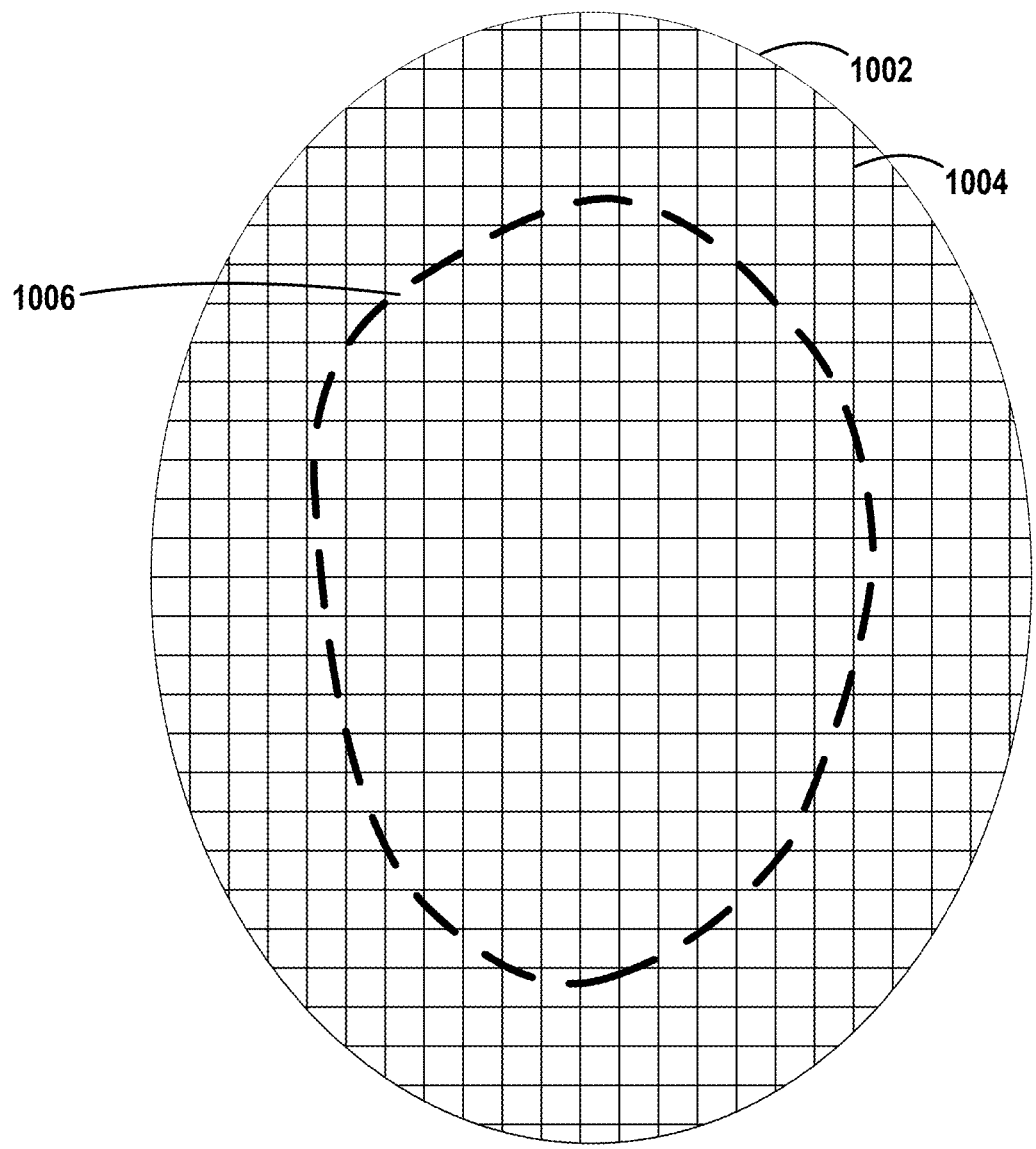
FIG. 10A is an illustration of a modification of an implant based on a three-dimensional shape of an anatomical feature, according to example embodiments.

FIG. 10A illustrates a modification of an implant 1002 based on a three-dimensional shape (e.g., the 3D shape 922 illustrated in FIG. 9C) of an anatomical feature, according to example embodiments. The modification of the implant 1002 may be a part of block 110 of method 100 (e.g., fabricating or modifying an implant based on the three-dimensional shape of the anatomical region), for example.

The implant 1002 may be a partially or wholly previously fabricated implant. For example, the partially or wholly previously fabricated implant may have been fabricated from polymer, metal, bioengineering material, titanium mesh, porous hydroxyapatite (HA), polyether ether ketone (PEEK), polymethylmethacrylate (PMMA), alloplastic, soft polymers, hard polymers, ceramics, and/or composites thereof. Taking the cranioplasty example, the implant 1002 may be a cranial implant partially or wholly previously fabricated based on standardized dimensions of human cranium. Alternatively, the implant 1002 may be a specialized, prefabricated implant (e.g., based on a mold or 3D model of the cranium of the patient undergoing the cranioplasty). For example, if the implant 1002 were a spinal implant (e.g., rather than a cranial implant), bony adapters of the implant 1002 may have been previously fabricated (e.g., based on CT or MRI data of a patient). Further, the implant 1002 may have grid lines 1004 or other guiding marks etched, printed, or projected (e.g., using one or more lasers or a lamp with a mask) on the implant 1002 in order to assist in the implant 1002 modification process.

Further, as illustrated by the dashed line, a 2D projection 1006 of an outline of the implant that will result after modification may be used. The 2D projection 1006 may correspond to the 3D shape 922 illustrated in FIG. 9C, for example. Additionally or alternatively, the 2D projection 1006 may be calculated (e.g., by a computing device) based on a previously determined 2D shape (e.g., the 2D shape 702 illustrated in FIG. 7D) and the projection plane (e.g., sagittal plane, transverse plane, coronal plane, or an intermediate plane lying in between the sagittal plane, the transverse plane, and/or the coronal plane) associated with the previously determined 2D shape. Further, the 2D projection 1006 may be printed, etched, or projected (e.g. using one or more lasers or a lamp with a mask) on the implant 1002. In addition to the 2D projection 1006 one or more positioning landmarks and/or orientation marks may be printed, etched, or projected on a stage on which modification of the implant 1002 may occur such that the implant 1002 can be oriented properly with respect to the stage. Additionally or alternatively, positioning landmarks and/or orientation marks may be printed, etched, or projected on the implant 1002 such that the implant 1002 can be oriented properly with respect to the stage.

Any portions of the implant 1002 lying outside of the 2D projection 1006 may then be removed from the implant 1002 (e.g., cut away by a saw or a high power laser that traces the periphery of the 2D projection 1006). Such a removal may be done by a surgeon (e.g., using a hand tool such as a reciprocating saw, a circulating saw, a hand saw, or other cutting tool), by a robot (e.g., using an associated cutting tool, such as a multi-axis cutting tool), or by a pattern tracing device with an associated cutting tool (e.g., a computer numerical control (CNC) device, such as a 3D CNC device, that is provided with the 2D projection 1006 as input).

In alternate embodiments, rather than modifying an earlier fabricated implant, an implant may be fabricated according to the 3D shape developed according to the methods described herein. Such a fabrication may be a part of block 110 of method 100 (e.g., fabricating or modifying an implant based on the three-dimensional shape of the anatomical feature), for example. In some embodiments, fabricating an implant according to the 3D shape may include printing the implant using additive manufacturing (e.g., 3D-printing). Printing the implant using additive manufacturing may include printing the device using a variety of materials (e.g., materials of differing densities to mimic various biological substrates within the patient as represented within the 3D shape). A variety of techniques may be used to print the implant using additive manufacturing, such as vat polymerization (e.g., using the PRO-JET 6000, 7000, or 8000 from 3D Systems Corp.), powder fusion (e.g., using EBM from Arcam AB), material extrusion (e.g., using FORTUS250 or FORTUS400 from Stratasys, Ltd.), powder binding (e.g., using PROJET 460 or 650 from 3D Systems Corp.), materials jetting (e.g., using OBJET500 or EDEN250 from Stratasys, Ltd.), or any other technique indicated by the ASTM F42 committee on additive manufacturing. In addition to or instead of additive manufacturing, other fabrication techniques could also be used (e.g., subtractive manufacturing, machining an implant from a block of substrate, creating an implantable balloon structure that can be filled with various viscous materials to impart shape and size, extrusion molding, casting (such as centrifugal, continuous, die, or evaporative-pattern casting), full-mold casting, lost-foam casting, investment casting (such as counter-gravity casting), lost-wax casting, low-pressure die casting, permanent-mold casting, plastic-mold casting, resin casting, sand casting, shell molding, vacuum molding, powder metallurgy, compression molding, transfer molding, extrusion molding, blow molding, dip molding, rotational molding, thermoforming molding, laminating molding, foam molding, shrink fitting molding, forging, rolling, extrusion, pressure shearing, stamping, bending, machining, joining, laser engineered net shaping, selective laser sintering, stereolithography, photolithography, fused-deposition molding, laminated-object manufacturing, direct-metal laser sintering, filament winder, or injection molding). It is understood that additional fabrication techniques are also possible.

Fabricating and/or modifying an implant may be performed during a surgery. For example, during a cranioplasty, a surgeon may resect an anatomical region of the patient, and then, using the methods described herein, fabricate or modify an implant based on a determined 3D shape of the anatomical feature. Then, prior to completing the surgery, the surgeon may implant the fabricated or modified implant into the patient. In this way, a single-stage surgery that includes both excision and implantation (e.g., a single-stage cranioplasty) may be performed.

Figure 10B:
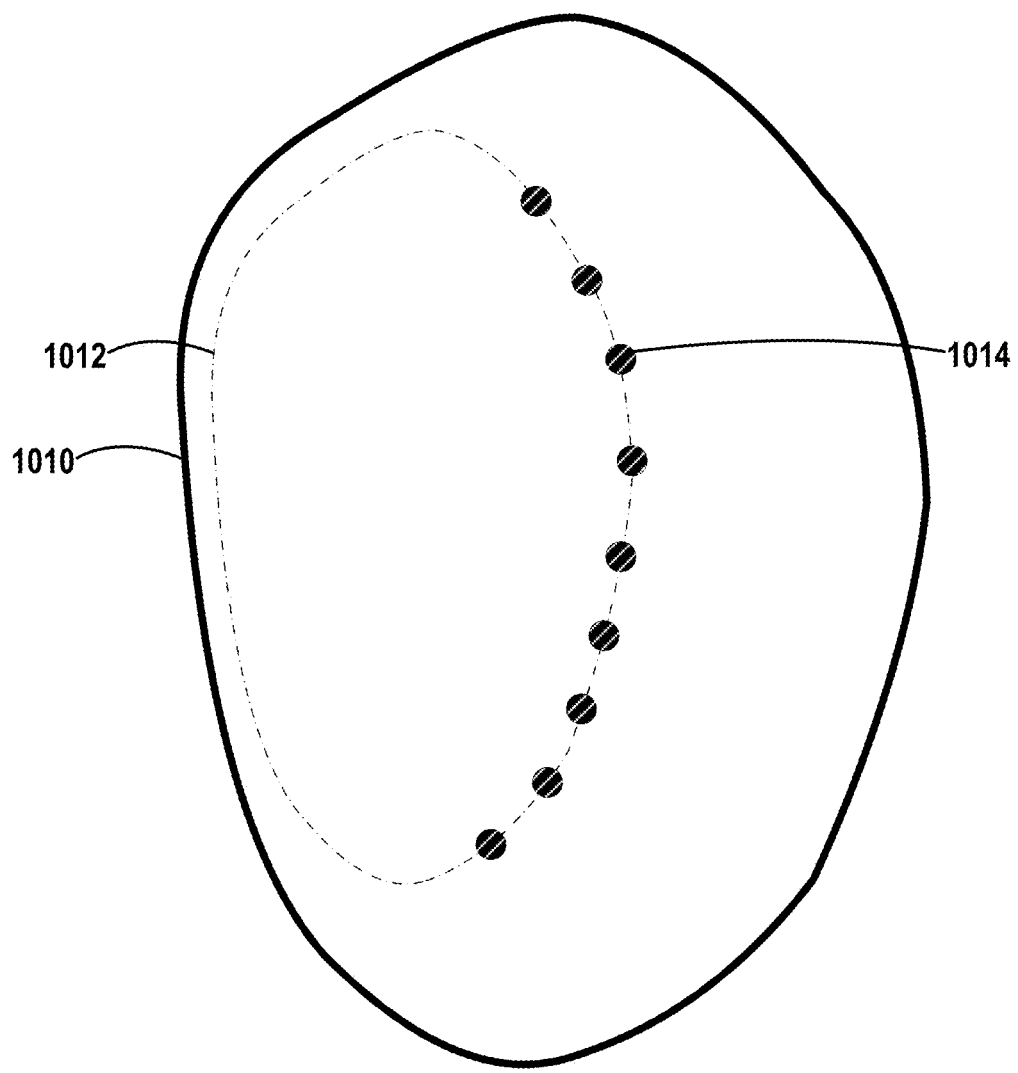
FIG. 10B is an illustration of an implant modified or fabricated based on a three-dimensional shape of an anatomical feature, according to example embodiments.

FIG. 10B is an illustration of an implant 1010 modified or fabricated based on a three-dimensional shape of an anatomical feature, according to example embodiments. The implant 1010 may have been fabricated or modified as part of block 110 of method 100 (e.g., fabricating or modifying an implant based on the three-dimensional shape of the anatomical feature), for example. The implant 1010 may include muscular guidelines 1012 and suture sites 1014 (e.g., suture holes) that indicate where an implant is to be attached to a patient. The muscular guidelines 1012 may be etched, printed, or projected onto the implant 1010. In addition, the suture sites 1014 may be etched onto, printed onto, or defined within (e.g., drilled through) the implant 1010. Further, the muscular guidelines 1012 and the suture sites 1014 may be based on a 3D model (e.g., a 3D model that includes Mill data) of a portion of the patient that contains the surgically resected anatomical region. For example, based on the 3D model, anastomosis sites may be determined between underlying muscle tissue and the portion of the cranium surgically resected or between one or more boney landmarks and the surgically resected anatomical region (e.g., muscle or tendons attached to such boney landmarks). Based on these anastomosis sites, an appropriate location for sutures sites 1014 may be determined. Further, for a surgeon's reference, the muscular guidelines 1012 may be indicated on the implant 1010.

Figure 10C:
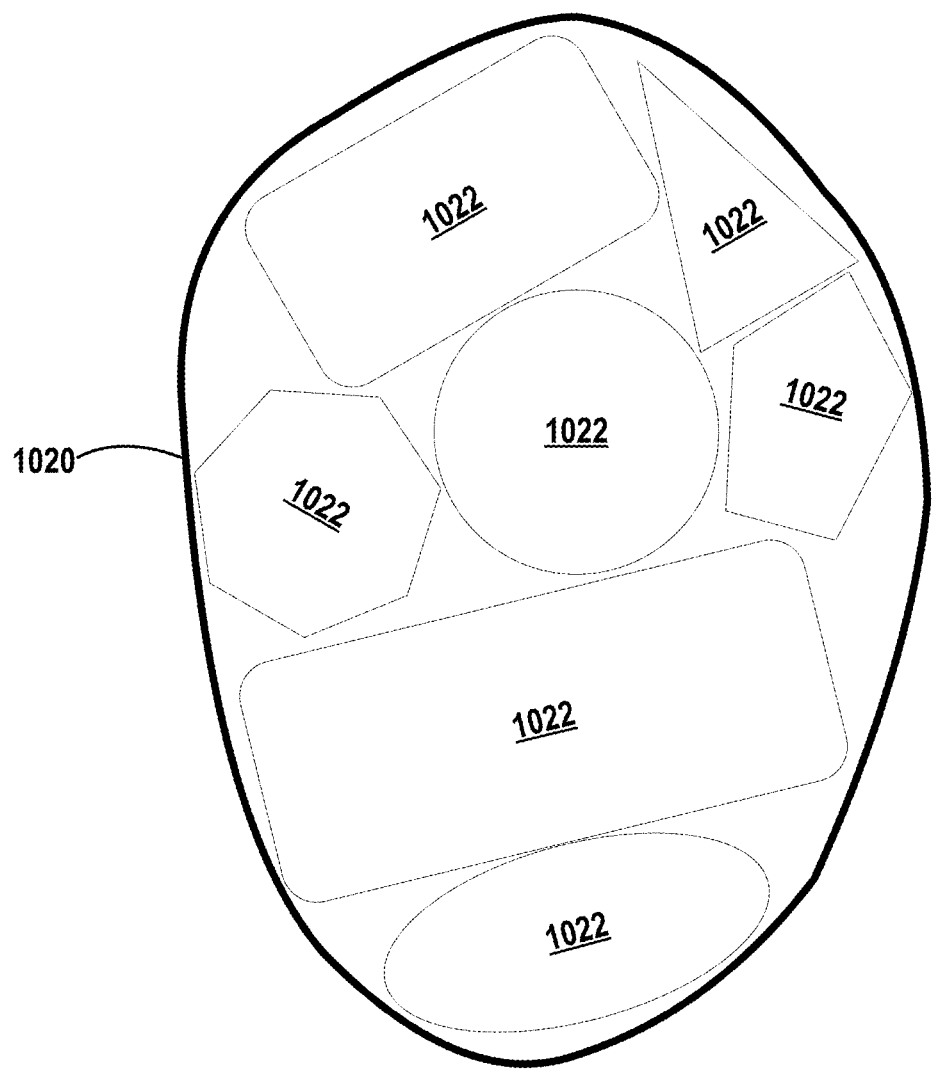
FIG. 10C is an illustration of a three-dimensional shape of an anatomical feature with defined locations configured to house medical devices usable to monitor or treat a patient, according to example embodiments.

FIG. 10C illustrates a three-dimensional shape of an anatomical feature with defined locations configured to house medical devices usable to monitor or treat a patient, according to example embodiments. The defined locations 1022 may be defined during block 108 of method 100 (e.g., determining, based on the two-dimensional shape of the anatomical feature and a three-dimensional model of a portion of the patient that contains the surgically resected anatomical region, a three-dimensional shape of the anatomical feature), for example. The defined locations 1022 may include recesses or hollowed out interior regions within the 3D shape 1020. The defined locations 1022 may be included in a projection onto an implant to be modified or such defined locations 1022 may be incorporated into an implant during a fabrication process (e.g., using additive manufacturing). As such, the defined locations 1022 may be included in an implant fabricated or modified using the 3D defined locations 1022.

In some embodiments, the defined locations 1022 may be shaped in such a way to accommodate specific medical devices. In other embodiments, the defined locations 1022 may be shaped in a standardized fashion so as to accommodate a variety of different medical devices. In various embodiments, the defined locations 1022 may accommodate a variety of medical devices, such as an Ommaya reservoir, one or more electrodes of a neurostimulator, one or more electrodes of a deep-brain stimulator, an intake to a fluid conduit leading to a cerebral balloon used to modulate blood flow or flow of spinal fluid, a medication pump, a microprocessor, a memory, a battery, a sensor, a heart pacemaker, a piece of spinal-fusion hardware, an intrauterine device (IUD), a piece of traumatic fracture repair hardware, a coronary stent, a tympanostomy tube, a stent, a vascular graft, an electrode, an infrared sensor, an infrared light, an accelerometer, a cellular device, a thermometer, an intracranial pressure monitor, a blood-pressure monitor, a blood-oxygen monitor, a vascular-flow monitor, a breast implant, an implantable cardioverter defibrillator (ICD), a spine screw, a spine rod, an artificial disk, a metal screw, a metal pin, a metal plate, a metal rod, or a stimulator.

Defining the position of one or more of the defined locations 1022 within the 3D shape 1020 of the anatomical feature configured to house the medical devices usable to monitor or treat the patient may include determining (e.g., by a computing device) optimized positions for the medical devices within the 3D shape 1020 of the anatomical feature. The optimized positions may be based on functions of the respective medical devices, shapes of the respective medical devices, sizes of the respective medical devices, orientations of the respective medical devices, a shape of the surgically resected anatomical portion, a size of the surgically resected anatomical portion, and/or an orientation of the surgically resected anatomical portion. For example, a plurality of defined locations 1022 for medical devices may be defined such that an optimized (e.g., maximized) number of medical devices may be located in the 3D shape 1020 (e.g., to maximize a 3D packing fraction of the volume within the 3D shape 1020). Such an optimization may include accounting for the size, shape, and/or function of each of the respective medical devices.

In other embodiments, the defined locations 1022 may be defined based on the functions of their intended respective medical devices alone. For example, in a 3D shape 1020 from which a cranial implant can be fabricated or modified, a defined location 1022 configured to house a neurostimulator or a deep-brain stimulator may be positioned near a center region of the 3D shape 1020 such that the respective medical device can access the biological substrate that it is intended to modify or treat, whereas a defined location 1022 configured to house a battery or memory may be positioned along a peripheral region of the 3D shape 1020.

Additionally or alternatively, one or more locations configured to house medical devices may be added (e.g., retrofitted) to an implant during fabrication or modification (e.g., by a surgeon), as opposed to or in addition to the defined locations 1022 within the 3D shape 1020 used to fabricate or modify the implant. Such additional locations configured to house medical devices may be added during block 110 of method 100 (e.g., fabricating or modifying an implant based on the three-dimensional shape of the anatomical feature), for example. For example, a location configured to house a battery may be added to the implant during fabrication or modification of the implant. Various locations configured to house various medical devices may be incorporated into the implant (e.g., by a surgeon) using a variety of tools (e.g., saws, drills, etc.).

In various embodiments described and contemplated herein, a modified and/or fabricated implant may result. In some embodiments, such an implant may be oriented (e.g., by a surgeon or a robot) relative to a portion of the patient that contains the surgically resected anatomical region (e.g., the cranium). Additionally or alternatively, the implant may then be implanted or installed (e.g., by a surgeon or robot) in the patient. Orienting the implant relative to the portion of the patient that contains the surgically resected anatomical region may include rotating or translating the implant.

III. EXAMPLE NON-TRANSITORY, COMPUTER-READABLE MEDIA

The methods described herein may be performed by a processor (e.g., the processor 332 illustrated in FIG. 3B) executing instructions stored within a non-transitory, computer-readable medium (e.g., the memory 334 illustrated in FIG. 3B). For example, the non-transitory, computer-readable medium having instructions stored therein, wherein the instructions, when executed by a process, comprise: receiving a registered plurality of intraoperative locations of a surgically resected anatomical region of a patient; generating, based on the registered plurality of intraoperative locations, a two-dimensional representation of the registered plurality of intraoperative locations; determining, based on the two-dimensional representation, a two-dimensional shape of an anatomical feature excised from the surgically resected anatomical region; determining, based on the two-dimensional shape of the anatomical feature and a three-dimensional model of a portion of the patient that contains the surgically resected anatomical region, a three-dimensional shape of the anatomical feature; and outputting the three-dimensional shape, wherein the three-dimensional shape is usable to fabricate or modify an implant such that the implant is implantable into the surgically resected anatomical region of the patient.

IV. EXAMPLE SYSTEMS

The methods described herein may be performed by a system (e.g., the system 300 illustrated in FIG. 3A). Such a system may include a device configured to register a plurality of intraoperative locations of a surgically resected anatomical region of a patient. In addition, the computing device may be configured to receive the registered plurality of intraoperative locations from the intraoperative probe; generate, based on the registered plurality of intraoperative locations, a two-dimensional representation of the registered plurality of intraoperative locations; determine, based on the two-dimensional representation, a two-dimensional shape of an anatomical feature excised from the surgically resected anatomical region; determine, based on the two-dimensional shape of the anatomical feature and a three-dimensional model of a portion of the patient that contains the surgically resected anatomical region, a three-dimensional shape of the anatomical feature; and output the three-dimensional shape, wherein the three-dimensional shape is usable to fabricate or modify an implant such that the implant is implantable into the surgically resected anatomical region of the patient.

V. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those described herein, will be apparent to those skilled in the art from the foregoing descriptions. Such modifications and variations are intended to fall within the scope of the appended claims.

The above detailed description describes various features and operations of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

With respect to any or all of the message flow diagrams, scenarios, and flow charts in the figures and as discussed herein, each step, block, operation, and/or communication can represent a processing of information and/or a transmission of information in accordance with example embodiments. Alternative embodiments are included within the scope of these example embodiments. In these alternative embodiments, for example, operations described as steps, blocks, transmissions, communications, requests, responses, and/or messages can be executed out of order from that shown or discussed, including substantially concurrently or in reverse order, depending on the functionality involved. Further, more or fewer blocks and/or operations can be used with any of the message flow diagrams, scenarios, and flow charts discussed herein, and these message flow diagrams, scenarios, and flow charts can be combined with one another, in part or in whole.

A step, block, or operation that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical operations or actions in the method or technique. The program code and/or related data can be stored on any type of computer-readable medium such as a storage device including read-only memory (ROM), random-access memory (RAM), a disk drive, a solid state drive, or another storage medium.

The computer-readable medium can also include non-transitory computer-readable media such as computer-readable media that store data for short periods of time like register memory and processor cache. The computer-readable media can further include non-transitory computer-readable media that store program code and/or data for longer periods of time. Thus, the computer-readable media may include secondary or persistent long term storage, like ROM, optical or magnetic disks, solid state drives, compact-disc read-only memory (CD-ROM), for example. The computer-readable media can also be any other volatile or non-volatile storage systems. A computer-readable medium can be considered a computer-readable storage medium, for example, or a tangible storage device.

Moreover, a step, block, or operation that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

What is claimed:
1. A method comprising:
registering a plurality of intraoperative locations of a surgically resected anatomical region of a patient;
generating, based on the registered plurality of intraoperative locations, a two-dimensional representation of the registered plurality of intraoperative locations;
determining, based on the two-dimensional representation, a two-dimensional shape of an anatomical feature excised from the surgically resected anatomical region;
determining, based on the two-dimensional shape of the anatomical feature and a three-dimensional model of a portion of the patient that contains the surgically resected anatomical region, a three-dimensional shape of the anatomical feature; and
fabricating or modifying an implant based on the three-dimensional shape of the anatomical feature,
wherein at least one of the plurality of intraoperative locations comprises a burr hole drilled during excision of the surgically resected anatomical region of the patient,
wherein at least one of the plurality of intraoperative locations comprises a point along which a cut was made between adjacent burr holes during excision of the surgically resected anatomical region of the patient, and
wherein determining the two-dimensional shape of the anatomical feature or determining the three-dimensional shape of the anatomical feature comprises defining edges of the two-dimensional shape or edges of the three-dimensional shape, respectively, based on the cut between adjacent burr holes.

2. The method of claim 1, further comprising:
orienting the implant relative to the portion of the patient that contains the surgically resected anatomical region; and
implanting the implant in the patient.

3. The method of claim 1, further comprising, prior to fabricating or modifying the implant, scaling the three-dimensional shape of the anatomical feature by a scaling factor such that the implant is smaller in size than the surgically resected anatomical region of the patient.

4. The method of claim 1, wherein the three-dimensional model comprises a computerized tomography (CT) model or a magnetic resonance imaging (MRI) model.

5. The method of claim 4, wherein determining the three-dimensional shape of the anatomical feature comprises performing a voxel-additive technique corresponding to regions of the three-dimensional model having a signal value above a threshold signal value that corresponds to bone.

6. The method of claim 1,
wherein registering the plurality of intraoperative locations of the surgically resected anatomical region of the patient comprises transmitting the plurality of intraoperative locations to a computing device,
wherein generating the two-dimensional representation of the registered plurality of intraoperative locations is performed by the computing device,
wherein determining the two-dimensional shape of the anatomical feature excised from the surgically resected anatomical region is performed by the computing device, and
wherein determining the three-dimensional shape of the anatomical feature is performed by the computing device.

7. The method of claim 6, wherein registering the plurality of intraoperative locations comprises, for each of the plurality of intraoperative locations:
placing an intraoperative probe at the respective intraoperative location; and
transmitting a three-dimensional location of the intraoperative probe to the computing device.

8. The method of claim 6,
wherein each of the plurality of intraoperative locations comprises a respective burr hole drilled during excision of the surgically resected anatomical region of the patient, and
wherein registering the plurality of intraoperative locations comprises, for each of the plurality of intraoperative locations:
placing an intraoperative probe at a first location on a circumference of a circle corresponding to the respective burr hole;
transmitting a first three-dimensional location of the intraoperative probe to the computing device;
placing the intraoperative probe at a second location on the circumference of the circle corresponding to the respective burr hole;
transmitting a second three-dimensional location of the intraoperative probe to the computing device; and
determining, by the computing device, a center of the circle corresponding to the respective burr hole.

9. The method of claim 8, wherein the second location is on a diameter of the circle corresponding to the respective burr hole opposite the first location.

10. The method of claim 6, wherein registering the plurality of intraoperative locations comprises:
receiving, by the computing device, an image of the surgically resected anatomical region of the patient; and
identifying, by the computing device according to a computer-vision algorithm, each of the plurality of intraoperative locations within the image.

11. The method of claim 6,
wherein generating the two-dimensional representation of the registered plurality of intraoperative locations comprises projecting each of the registered intraoperative locations onto a two-dimensional plane, and
wherein determining the two-dimensional shape of the anatomical feature comprises:
identifying, by the computing device, two or more closed polygons each having as their vertices each of the registered plurality of intraoperative locations projected onto the two-dimensional plane;
displaying, by the computing device, each of the two or more closed polygons; and
receiving, by the computing device, a selection of which of the two or more closed polygons corresponds to the two-dimensional shape of the anatomical feature excised from the surgically resected anatomical region.

12. The method of claim 6,
wherein generating the two-dimensional representation of the registered plurality of intraoperative locations comprises projecting each of the registered intraoperative locations onto a two-dimensional plane, and
wherein determining the two-dimensional shape of the anatomical feature comprises:
identifying, by the computing device, two or more closed polygons each having as their vertices each of the registered intraoperative locations projected onto the two-dimensional plane;
comparing, by the computing device, each of the two or more closed polygons to previously determined two-dimensional shapes of other anatomical features excised from other surgically resected anatomical regions; and
determining, by the computing device based on the comparison, which of the two or more closed polygons have a threshold probability of corresponding to the two-dimensional shape of the anatomical feature excised from the surgically resected anatomical region.

13. The method of claim 12, wherein the other anatomical features excised from the other surgically resected anatomical regions correspond to additional anatomical features excised from one or more additional surgically resected anatomical regions of the patient.

14. The method of claim 12, wherein the other anatomical features excised from the other surgically resected anatomical regions correspond to similar anatomical features excised from one or more similar surgically resected anatomical regions of one or more other patients.

15. The method of claim 12,
wherein the other anatomical features excised from the other surgically resected anatomical regions were excised by a surgeon, and
wherein the surgeon also excised the anatomical feature excised from the surgically resected anatomical region of the patient.

16. The method of claim 1,
wherein generating the two-dimensional representation of the registered plurality of intraoperative locations comprises projecting each of the registered intraoperative locations onto a two-dimensional plane,
wherein determining the two-dimensional shape of the anatomical feature comprises identifying a closed polygon having as its vertices each of the registered intraoperative locations projected onto the two-dimensional plane, and
wherein no edges of the closed polygon intersect one another.

17. The method of claim 1, wherein the anatomical feature excised from the surgically resected anatomical region is a portion of a cranium of the patient.

18. The method of claim 1, wherein the anatomical feature excised from the surgically resected anatomical region is a maxillofacial portion of the patient.

19. The method of claim 1, further comprising defining, within the three-dimensional shape of the anatomical feature, a location configured to house a medical device usable to monitor or treat the patient.

20. The method of claim 19, wherein defining, within the three-dimensional shape of the anatomical feature, the location configured to house the medical device usable to monitor or treat the patient comprises determining an optimized position for the medical device within the three-dimensional shape of the anatomical feature based on a function of the medical device, a shape of the medical device, a size of the medical device, an orientation of the medical device, a shape of the surgically resected anatomical portion, a size of the surgically resected anatomical portion, or an orientation of the surgically resected anatomical portion.

21. The method of claim 19, wherein the medical device comprises an Ommaya reservoir, one or more electrodes of a neurostimulator, one or more electrodes of a deep-brain stimulator, an intake to a fluid conduit leading to a cerebral balloon used to modulate blood flow or flow of spinal fluid, a medication pump, a microprocessor, a memory, a battery, a sensor, a heart pacemaker, a piece of spinal-fusion hardware, an intrauterine device (IUD), a piece of traumatic fracture repair hardware, a coronary stent, a tympanostomy tube, a stent, a vascular graft, an electrode, an infrared sensor, an infrared light, an accelerometer, a cellular device, a thermometer, an intracranial pressure monitor, a blood-pressure monitor, a blood-oxygen monitor, a vascular-flow monitor, a breast implant, an implantable cardioverter defibrillator (ICD), a spine screw, a spine rod, an artificial disk, a metal screw, a metal pin, a metal plate, a metal rod, or a stimulator.

22. The method of claim 1, wherein fabricating or modifying the implant comprises incorporating, based on the three-dimensional model, materials of differing densities into the implant to mimic differing biological substrates of the anatomical feature excised from the surgically resected anatomical region.

23. The method of claim 22, wherein at least one of the biological substrates comprises soft tissue.

24. The method of claim 1, wherein modifying the implant based on the three-dimensional shape of the anatomical feature comprises:
projecting an outline of the anatomical feature onto the implant; and
removing portions of the implant lying outside of the outline of the anatomical feature projected onto the implant.

25. The method of claim 1, wherein fabricating the implant based on the three-dimensional shape of the anatomical feature comprises printing the implant using additive manufacturing.

* * * * *